US008222039B2

(12) United States Patent
Monthony et al.

(10) Patent No.: US 8,222,039 B2
(45) Date of Patent: Jul. 17, 2012

(54) PROCESS FOR PURIFICATION OF WATER SOLUBLE POLYMERS

(75) Inventors: James F. Monthony, Cornwall (CA); Li Yang, Charlottetown (CA); Kurt E. Kershaw, Stanhope (CA); Christopher D. Winslow, Cornwall (CA); John G. Riley, Charlottetown (CA)

(73) Assignee: Biovectra Inc., Charlottetown, Prince Edward Island (CA)

( * ) Notice: Subject to any disclaimer, the term of this patent is extended or adjusted under 35 U.S.C. 154(b) by 127 days.

(21) Appl. No.: 12/528,304

(22) PCT Filed: Feb. 22, 2007

(86) PCT No.: PCT/CA2007/000272
§ 371 (c)(1),
(2), (4) Date: Aug. 21, 2009

(87) PCT Pub. No.: WO2008/101311
PCT Pub. Date: Aug. 28, 2008

(65) Prior Publication Data
US 2010/0323452 A1    Dec. 23, 2010

(51) Int. Cl.
*C08G 65/329* (2006.01)
(52) U.S. Cl. .......................... 436/85; 436/161; 436/178
(58) Field of Classification Search .................. 436/85, 436/8, 17, 161, 175, 177, 178; 528/421, 528/425; 525/523, 533
See application file for complete search history.

(56) References Cited

U.S. PATENT DOCUMENTS

| | | | |
|---|---|---|---|
| 5,298,410 A | 3/1994 | Phillips et al. | |
| 5,672,662 A | 9/1997 | Harris et al. | |
| 5,747,639 A | 5/1998 | Seely | |
| 5,935,564 A | 8/1999 | Seely | |
| 6,245,238 B1 | 6/2001 | Agner | |
| 6,448,369 B1 | 9/2002 | Bentley et al. | |
| 6,455,639 B1 | 9/2002 | Yasukohchi et al. | |
| 6,576,134 B1 | 6/2003 | Agner | |
| 2004/0062746 A1 | 4/2004 | Martinez et al. | |
| 2005/0054816 A1* | 3/2005 | McManus et al. | 528/425 |
| 2006/0045866 A1 | 3/2006 | Chappelow et al. | |
| 2006/0249457 A1 | 11/2006 | Van Alstine et al. | |

OTHER PUBLICATIONS

Monfardini, Cristina et al. "A branched monomethoxypoly(ethylene glycol) for protein modification." Bioconjugate Chemistry (1995) 6 62-69.*
Hajos, Peter et al. "Retention behaviours and separation of carboxylic acids by ion-exchange chromatography." Journal of Chromatography B (1998) 717 27-38.*
Lapienis, Grzegorz et al. "Preparation of monomethyl ethers of poly (ethylene glycol)s free of the poly(ethylene glycol)." Journal of Bioactive and Biocompatible Polymers (2001) 16 206-220.*
Seely, James E. et al. "Use of ion-exchange chromatography and hydrophobic interaction chromatography in the preparation and recovery of polyethylene glycol-linked proteins." Journal of Chromatography A (2001) 908 235-241.*
Drioli et al., Pure, homo-bifunctional poly(ethylene glycol) orthogonally protected: synthesis and characterisation, Reactive & Functional Polymers, 2001, vol. 48, pp. 119-128.
Hodges et al., Preparative Purification of Peptides by Reversed-Phase Chromatography: Sample Displacement Mode Versus Gradient Elution Mode, Journal of Chromatography, 1988, vol. 444, pp. 349-362.
Oudhoff et al., Characterization of polyethylene glycols and polypropylene glycols by capillary zone electrophoresis and micellar electrokinetic chromatography, Journal of Chromatography A, 2003, vol. 985, pp. 479-491.
Roberts et al., Chemistry for peptide and protein PEGylation, Advanced Drug Delivery Reviews, 2002, vol. 54, pp. 459-476.
Rosendahl et al., Site-Specific Protein PEGylation: Application to Cysteine Analogs of Recombinant Human Granulocyte Colony-Stimulating Factor, BioProcess International, Apr. 2005, pp. 52-60.
Sang-Heon Lee et al , Synthesis, Characterization, and Pharmacokinetic Studies of PEGylated Glucagon-like Peptide-1, Bioconjugate Chem., 2005, vol. 16, Issue 2, pp. 377-382.
Zalipsky, Synthesis of an End-Group Functionalized Polyethylene Glycol-Lipid Conjugate for Preparation of Polymer-Grafted Liposomes, Bioconjugate Chem., 1993, vol. 4, Issue 4, pp. 296-299.
Zalipsky, Functionalized Poly(ethylene glycol) for Preparation of Biologically Relevant Conjugates, Bioconjugate Bioconjugate Chem., 1995, vol. 6, Issue 2, pp. 150-165.
Zalipsky et al., Preparation of Polyethyelene Glycol Derivatives with Two Different Functaional Groups at the Termini, Poly. Prep. American Chemical Society Div. Polym. Chem., 1986, vol. 27(1), pp. 1-2.
Zalipsky et al., Facile Synthesis of (alpha)-Hydroxy-(omega)—Carboxymethylpolyethylene Oxide, Journal of Bioactive and Compatible Polymers, Apr. 1990, vol. 5, pp. 227-231.

* cited by examiner

*Primary Examiner* — Yelena G Gakh
*Assistant Examiner* — Christopher A Hixson
(74) *Attorney, Agent, or Firm* — Knobbe, Martens, Olson & Bear, LLP

(57) ABSTRACT

A process for purification of water soluble polymers is provided. A polymer of interest can be separated from a mixture of polymers, provided the polymer of interest differs from other polymers in the mixture in the number of reactive terminal groups. The process involves derivatizing polymers at the reactive terminal groups with a derivatizing molecule, bearing either (i) two or three cationic or anionic ionizable groups, and a group capable of covalent bonding to the reactive terminal groups or (ii) three or four ionizable groups, at least one of which is capable of covalent bonding to the reactive terminal groups; followed by ion exchange. The process allows removal of PEG from MPEG, and can be used for polymers having an average size greater than 9,000 Da Derivatization may be reversible in order to allow re-use of recovered contaminant polymers.

26 Claims, 21 Drawing Sheets

MPEG 20 000 Da Diacid Unpurified

| Peak name | Retention time (min) | Area % |
|---|---|---|
| 1. Neutral material | 1.17 | 4.70 |
| 2. MPEG benzene tricarboxylic acid ester; isomer 1 | 4.45 | 37.24 |
| 3. MPEG benzene tricarboxylic acid ester; isomer 2 | 5.01 | 55.48 |
| 4. PEG α,ω-bis-(benzene tricarboxylic acid ester) | 7.95 | 2.59 |

MPEG 20,000 Da Purification - Fraction 4

| Peak name | Retention time (min) | Area % |
|---|---|---|
| 1. Neutral material | 1.81 | 0.07 |
| 2. MPEG benzene tricarboxylic acid ester isomer 1 | 4.47 | 46.97 |
| 3. MPEG benzene tricarboxylic acid ester isomer 2 | 5.03 | 52.96 |

MPEG 10,000 Da Benzene Tricarboxylic Acid Esters Before Purification

| 1. Neutral material | 1.22 | 3.14 |
| --- | --- | --- |
| 2. MPEG benzene tricarboxylic acid ester isomer 1 | 5.99 | 37.01 |
| 3. MPEG benzene tricarboxylic acid ester isomer 2 | 7.32 | 50.46 |
| 4. PEG α,ω-*bis*-(benzene tricarboxylic acid ester) | 12.40 | 9.40 |

Purified MPEG 10,000 Da Benzene Tricarboxylic Acid Ester

| Peak name | Retention time (min) | Area % |
|---|---|---|
| 1. Neutral material | 4.27 | 4.48 |
| 2. MPEG benzene tricarboxylic acid ester isomer 1 | 19.41 | 32.81 |
| 3. MPEG benzene tricarboxylic acid ester isomer 2 | 20.19 | 62.71 |

Unpurified MPEG 30,000 Da Benzene Tricarboxylic Acid Esters

| Peak name | Retention time (min) | Area % |
|---|---|---|
| 1. Neutral material | 1.13 | 6.65 |
| 2. MPEG benzene tricarboxylic acid ester isomer 1 | 4.23 | 34.33 |
| 3. MPEG benzene tricarboxylic acid ester isomer 2 | 4.78 | 52.56 |
| 4. PEG α,ω-bis-(benzene tricarboxylic acid ester) | 7.01 | 6.46 |

MPEG 30,000 Da benzene tetracarboxylic acid ester (purified)

| Peak name | Retention time (min) | Area % |
|---|---|---|
| 1. Neutral material | 4.04 | 2.73 |
| 2. MPEG benzene tetracarboxylic acid ester | 29.33 | 97.27 |

Overlay MPEG 20,000 Da succinate ester / PEG 35,000 Da α,ω-*bis*-succinate ester Overlay MPEG 20 000 Da benzene tricarboxylic acid ester / PEG 35 000 Da α,ω-*bis*-(benzene tricarboxylic acid ester)

Diacid Thiol Addition Product

Maleimide Ring Opening to Maleamic Acid Monoacid

MPEG Maleimide Analysis

| Peak name | Retention time (min) | Area % |
|---|---|---|
| 1. Neutral material | 1.14 | 7.46 |
| 2. MPEG maleamic acid (ring open starting material) [monoanion] | 2.56 | 3.95 |
| 3. MPEG maleimide mercaptosuccinate addition product [dianion] | 4.11 | 80.88 |
| 4. MPEG maleamic acid mercaptosuccinic acid addition product [trianion] | 7.47 | 7.71 |

Overlay MPEG 20 000 Da Sulfosuccinic Acid Amide (Diacid) / MPEG 20 000 Da Benzene Dicarboxylic Acid Ester (Diacid)

**Overlay of monoamine MPEG and Diamine MPEG.
MPEG 30,000 Da methoxybenzylamine (monoamine) &
MPEG 30,000 Da dimethylaminopropylamine (diamine)**

Synthesis and Purification of Poly(ethylene glycol) Mono Alkyl Ethers

Poly(ethylene glycol) monoethyl ether, EtO-PEG

Poly(ethylene glycol) monomethyl ether, MPEG

Analysis of 35,000 Da MPEG Benzene Tricarboxylic Acid Ester Synthesized from 35,000 Da PEG

PROCESS FOR PURIFICATION OF WATER SOLUBLE POLYMERS

This application is U.S. National Phase of International Application PCT/CA2007/000272, filed Feb. 22, 2007 designating the U.S., and published in English as WO 2008/101311 on Aug. 28, 2008.

FIELD OF THE INVENTION

The invention relates generally to a chemical purification process, and more particularly, to a process for separation of water soluble polymers from impurities arising in their production.

BACKGROUND OF THE INVENTION

Numerous challenges arise in production and purification of water soluble polymeric materials, not the least of which is the separation of specific polymers from impurities arising from synthetic processes. Following certain synthetic processes, polymers having one or more chemically reactive end groups must be separated from similar molecules having either a greater or lesser number of such reactive end groups.

There exists a specific need for the production of water soluble polymers of high purity that can react to form a single chemical bond with other target molecules. A common difficulty in these processes is the presence of contaminant polymer molecules having more than one reactive termini, that can form bonds to more than one of the target molecules or which form bonds to more than one different molecular species. In certain other applications, multiple bonds are the desired outcome and the removal of material with only a single reactive termini would improve the performance of such multiply reactive polymers.

Pharmaceutical science has undergone a rapid expansion in the types of agents used in treatment of disease and/or other disorders. Protein drugs are produced and marketed for the treatment of several human disease states. Small molecules are designed and developed that specifically interact with receptor sites found on cells, tumors, organs and the like. The effective and efficient delivery of materials has become an increasingly important aspect of the drug development and utilization process. Water soluble polymers such as poly(ethylene glycol) polymers (PEG polymers) and the monovalent mono ether derivatives of poly(ethylene glycol) such as monomethoxy poly(ethylene glycol) or MPEG polymers are valuable agents in the delivery and formulation of an ever increasing number of drug products. The structure of simple linear PEG and MPEG are shown in Formula 1A and Formula 1B respectively.

1A: PEG

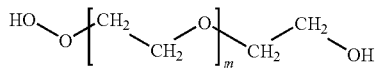

1B: MPEG

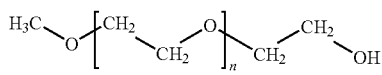

In some applications, both ends of a PEG polymer are utilized, for example, to couple a radioactively labeled material via the intervening polymer chain to a small molecule or small peptide that specifically binds to a cell receptor in vivo. These applications require material that can be manipulated differently at the two (or more) termini present.

Other applications utilize a MPEG material to increase the effective molecular weight and decrease the rate of elimination of a peptide or protein drug once introduced in vivo. In such applications it is highly preferred to have only a single reactive end and therefore only a single chemical bond formed between the polymer and the protein or peptide.

While it is in such pharmaceutical applications that the current invention will likely find its greatest application, the general difficulty in purification of polymeric materials after chemical modifications that effect only their end groups makes it beneficial to start with as homogenous (pure) a polymer as possible whenever such materials are to be modified. Further, the reversible nature of the modifications of the current invention and the manner in which it can enable purification of polymers not normally capable of ready purification has great utility whenever the preparation of modified forms of a water soluble polymer material is undertaken, even if the original polymeric material was quite pure.

The use of poly(ethylene glycol), PEG, and its monosubstituted methyl ether, MPEG, to conjugate to a protein has become so commonly practiced that the term PEGylation has been adopted to describe such protein conjugation. A search of the US patent application database of published applications for the term PEGylation gave over 2900 citations. Six of these applications contained PEGylation in the title, suggesting that such modifications to proteins and other molecules has become routine. Roberts et al. provides a review entitled "Chemistry for peptide and protein PEGylation," in Advanced Drug Delivery Reviews 54 (2002) 459-476. An example of the modification of a biologically active peptide can be found in Lee et al., "Synthesis, Characterization, and Pharmacokinetic Studies of PEGylated Glucagon-like Peptide-1," Bioconjugate Chemistry 16, (2005) 377-382. Rosendahl et al. describes site-specific protein PEGylation in BioProcess International, April 2005, 52-62. There is a demand for water soluble polymers such as poly(ethylene glycol) and MPEG derivatives of the highest purity.

In the preparation of MPEG polymers, the monofunctional product is produced by initiating the polymerization of ethylene oxide with, for example, sodium methoxide. Methyl ethers of ethylene glycol or of diethylene glycol can also be used. It is known that the synthesis of MPEG often produces a product with significant contamination with PEG. This PEG arises due to the presence of water in the polymerization mixture. Further, it is known that the ethylene oxide utilized in the preparation of MPEG polymer usually contains trace amounts of water as an impurity. This water can lead to the formation of additional PEG contaminant in a MPEG synthesis, as discussed in U.S. Pat. No. 6,448,369 to Bentley et al. U.S. Pat. No. 6,448,369 describes an alternative to the purification of the polymer in the preparation of heterobifunctional PEG derivatives in which the impurity is reacted to a relatively inert form by chemical reaction with a blocking group such that the impurity will not react with target molecules. While representing a moderately pragmatic approach for the short term, the use of such mixtures and the necessity of their remaining inert throughout use as well as the need to ultimately separate PEGylated materials from unreacted PEG reagents makes this approach less than ideal. Pharmaceutical usages would not benefit from the presence of such polymeric impurities. U.S. Pat. No. 6,448,369 also refers to chromatographic methods of Zalipshky in Bioconjugate Chemistry, 6 (1995) 150-165 and U.S. Pat. Nos. 5,747,639 and 5,935,564 to Seely, as applicable to the purification of polymeric PEGylation materials, but characterized such methods as tedious and having little value for useful commercial production.

U.S. Pat. Nos. 5,747,639 and 5,935,564 relate to hydrophobic interaction chromatography, which requires the use of high salt concentrations, expensive specialty media, and tends to have low binding capacities for the types of media utilized. The highest loading capacity disclosed in these patents involves the application of 8 mg of a PEG based material for each ml of chromatographic medium used, typically 3 mg of PEG per ml of material.

U.S. Pat. No. 5,747,639 describes PEG and the production of symmetrical bi-functional PEG derivatives. Separations described involve removal of PEG and PEG derivatives having only one end of the PEG derivatized with the desired moiety while the other end is present as an unmodified hydroxyl group. No route for separating reacted from unreacted MPEG materials is provided, and there is no suggestion of a method for purification and recovery of MPEG for use in the preparation of other derivatives.

An ion exchange separation of PEG derivative is described by Zalipsky in "*Synthesis of an End-Group Functionalized Polyethylene Glycol-Lipid Conjugate for Preparation of Polymer-Grafted Liposomes*", Bioconjugate Chem. 4, 296-299 (1993) wherein derivatives are prepared that possess a carboxylic acid group at one or both ends. The anionic forms of these derivatives allow separation of PEG, the homobifunctional PEG diacid and the mono-substituted PEG monoacid. MPEG materials are not described and the method is intended for PEG materials that are 4,000 Da or less in size.

U.S. Pat. No. 5,298,410 to Phillips teaches that the ion exchange methods of Zalipsky et al. (Journal of Bioactive and Compatible Polymers, Vol. 5, April 1990, pp. 227-231) fail when higher molecular weight PEGs are used. This patent discloses the preparation of an MPEG fraction free of PEG at a molecular weight of 5,000 Da. Although there is some suggestion that higher molecular weight MPEG can be purified by the disclosed reverse phase chromatography methods, no examples are given, and the maximum size of the material referred to is 15,000 Da. The methodology described involves preparation of a reversible derivative of MPEG and the contaminating PEG. Triphenyl methyl (or trityl) ether derivatives are used and the method employs expensive acetonitrile containing elutants and expensive reverse phase silica chromatographic media. This patent describes the ion exchange purification of a mono-acid derivative of PEG made with PEG 2,000. A similar PEG based purification of mono-carboxylate substituted PEG from PEG and the di-carboxylate form is described in U.S. Pat. No. 5,672,662 to Harris and Kozlowski.

An ion exchange separation of PEG based materials that proceeds based on the substitution of one end of the PEG with a DMT (dimethoxytrityl) ether group is described by Drioli et al. (Reactive & Functional Polymers 48 (2001) 119-128). The omission of the DMT group allows small scale purification of a PEG mono-succinate from a PEG di-succinate, but with noted difficulty and overlap of the products. The DMT group was a key in the more successful routes and was added first in sufficient quantity to avoid, at least statistically, the presence in the final mixture of any starting free PEG. A subsequent reaction with a large excess of succinic anhydride allows the preparation of the DMT-PEG derivative free from PEG-bis succinic acid. This approach is not applicable to the preparation of MPEG free of PEG and was not demonstrated with PEG above 6,000 Da.

An alternative approach can be taken in which PEG derivatives are prepared with only one end of the PEG functionalized for conjugation to protein (or other material), instead of using MPEG mono-functional derivatives. U.S. Patent Application 2005/054816 by McManus et al. states that the current methods of preparing activated PEGs, particularly monosubstituted activated PEGs, are unsatisfactory because of reliance on the use of expensive MPEG starting material, containing contaminant PEG diol. Conventional synthetic approaches to avoid diol formation are complicated and can still result in the formation of detectable amounts of byproducts.

While U.S. Patent Application 2005/054816 demonstrates the purification of MPEG materials substantially free of PEG, it does so only when the PEG starting material has been partially reacted. Mixtures formed from a PEG are essentially of a common average molecular weight and have a homogeneous distribution of molecular weights. Example 7 of U.S. Patent Application 2005/054816 describes the use of a typical MPEG of 20,000 Da that contains 6 wt % of PEG-diol having a molecular weight of about 40,000 Da. A covalently bonded carboxylic acid group is produced in a three step reaction yielding a mixture that is 6% PEG (40,000 Da)-dipropionic acid and MPEG (20,000 Da)-propionic acid (91%) and MPEG (20,000 Da) (3%). This is purified using a chromatographic process to separate the neutral PEG materials from the mono-acid and the diacid forms. A complex chromatographic system is employed for separation, which uses a limited amount of media to provide some measure of selectivity for the charged species formed. In the final example, the same media is used in both the pre-column and the column. Thus, the basis of separation seems to be the marginal difference in binding between the mono-substituted and di-substituted material. In each case it is noted that the pre-column contains both the di-substituted PEG product and the mono-substituted desired product without providing much quantitative data on the relative yields. FIG. 4D of this publication illustrates that material bound to the pre-column is 80% mono and only about 20% PEG di-acid.

U.S. Patent Application 2005/054816 teaches the alkylation or substitution of the PEG alcohol or anion thereof with a halide, vinyl, tosyl or mesyl group wherein an ether type bond is formed between the PEG oxygen and the functionalizing reagent.

Chromatographic methods known as sample displacement chromatography allow purification of peptides by reversed-phase chromatography in a sample displacement mode rather than a gradient elution mode, as described Hodges et al. (J. Chromatogr. 1988; 444,349-62), or in U.S. Pat. No. 6,576, 134 and U.S. Pat. No. 6,245,238 to Agner.

In U.S. Patent Application 2004/0062746 to Martinez et al., a method is described to prepare PEG having one reactive end and the other end as a hydroxyl group, not as a blocked end group such as with an MPEG derivative. Reverse phase chromatography is used to separate mixtures of PEG materials differing in their end group compositions, but no use of ion exchange is taught.

Oudhoff et al. described electrophoretic characterization and analysis of PEG using multiply charged derivative compounds in "Characterization of polyethylene glycols and polypropylene glycols by capillary zone electrophoresis and micellar electrokinetic chromatography." J Chromatogr A. 985, 479-91(2003). The additional charge introduced using such materials as described by Oudhoff et al., as compared to a simple monoacid derivative, demonstrates only a standard mass to charge ratio increase in electrophoretic mobility and provides a more rapid separation. While this shortens the time of the analysis, it is not a major improvement in the analytical separation of species. The capillary electrophoresis methodology described is only an analytical method, and has no preparative applications. MPEG materials were not assessed.

One approach to obtaining high purity MPEG has been to exercise extraordinary care in the synthesis of MPEG from ethylene oxide and a methoxide initiator. U.S. Pat. No. 6,455,639 to Yasukohchi follows this route of production directly from oxirane materials that are greater than 98% pure. Statements in this patent suggest it is not possible to achieve a purity of greater than 98% by industrial separation/purification processes such as fractional liquid chromatography.

There remains a continuing need for high purity MPEG with very low PEG content, as well as a method to produce such high purity MPEG.

SUMMARY OF THE INVENTION

The invention provides processes that allow separation of water-soluble polymers in a way that overcomes one or more disadvantage of prior art processes.

According to one embodiment of the invention, there is provided a process for purification of a water soluble polymer of interest from an initial mixture of polymers, wherein the polymer of interest contains a different number of reactive terminal groups than other polymers in the mixture. The process comprises reacting the initial mixture of polymers with a derivatizing molecule to form a reacted polymer mixture, said derivatizing molecule comprising (i) 2 or 3 ionizable groups and a group available for covalent bonding with the reactive terminal groups; or (ii) 3 or 4 ionizable groups, at least one of the ionizable groups being available for covalent bonding with the reactive terminal groups; subjecting the reacted polymer mixture to ion exchange; and collecting a fraction containing the polymer of interest.

According to a further embodiment of the invention, there is provided a process for separating one or more contaminant polymer from a polymer of interest, wherein the polymer of interest comprises n reactive terminal groups and the contaminant polymer comprises m reactive terminal groups, wherein n and m are whole numbers and n≠m. The process comprises reacting the reactive terminal groups with a derivatizing molecule comprising (i) 2 or 3 ionizable groups and a group available for reversible covalent bonding with the reactive terminal groups; or (ii) 3 or 4 ionizable groups, at least one of the ionizable groups being available for reversible covalent bonding with the reactive terminal groups; and separating the contaminant polymer from the polymer of interest using ion exchange chromatography.

Thus, embodiments of the processes of the invention permit collection of a highly purified mono alkyl ether end capped poly(ethylene glycol), separated from contaminant polymers, such as poly(ethylene glycol). The highly purified mono alkyl ether end capped poly(ethylene glycol) obtained may have less than 1% poly(ethylene glycol) content. This level of purity was previously unattainable or was difficult to obtain for endcapped poly(ethylene glycol) produced by the polymerization of ethylene oxide using other processes.

An inventive polymer mixture is obtained according to an embodiment of the invention. The mixture comprises poly(ethylene glycol) polymers having the general formulae $R_1$—O-PEG-O—$R_1$ and $R_1$—O-PEG-O—$R_2$, wherein —$R_1$ comprises a di-anion, a tri-anion, a di-cation or a tri-cation; and —$R_2$ is a straight-chain alkyl group containing 1 to 4 carbon atoms, a benzyl group or a triphenylmethyl group.

Further, an embodiment of the invention provides a method for analysis of the presence of more than one water soluble polymer in an initial mixture, wherein each polymer to be assessed has a different number of reactive terminal groups. The method comprising the steps of reacting the initial mixture with a derivatizing molecule to form a reacted polymer mixture; said derivatizing molecule comprising (i) 2 or 3 ionizable groups and a group available for covalent bonding with the reactive terminal groups; or (ii) 3 or 4 ionizable groups, at least one of the ionizable groups being available for covalent bonding with the reactive terminal groups; or (iii) 2, 3 or 4 amine groups, one of the amine groups being available for covalent bonding with a reactive terminal group consisting of an aldehyde or —$CH_2$—X wherein X is a halide, sulfonic acid ester or other leaving group; subjecting the reacted polymer mixture to ion exchange chromatography; and evaluating polymer composition of the reacted polymer mixture.

Additionally, according to an embodiment of the invention, there is provided a process for preparation of poly(ethylene glycol) monoethyl ether (Eta-PEG) from poly(ethylene glycol) (PEG). The method comprises heating PEG with toluene, pyridine, and $SOCl_2$ to form a polymeric mixture; reacting the polymeric mixture with ethanol, KBr and KOH to form a mixture containing EtO-PEG; reacting the mixture containing EtO-PEG with a derivatizing molecule Q to form a mixture containing a derivatized polymer EtO-PEG-Q; said derivatizing molecule comprising (i) 2 or 3 ionizable groups and a group available for covalent bonding with a terminal hydroxy group of EtO-PEG; or (ii) 3 or 4 ionizable groups, at least one of the ionizable groups being available for covalent bonding with a terminal hydroxy group of EtO-PEG; subjecting the mixture containing derivatized polymer EtO-PEG-Q to ion exchange; collecting a fraction containing the derivatized polymer EtO-PEG-Q; and removing the derivatizing molecule from the derivatized polymer EtO-PEG-Q to form poly(ethylene glycol) monoethyl ether. The product formed as a result of this process, a purified EtO-PEG, is also considered an embodiment of the invention. The EtO-PEG product may comprise less than 2% contaminant polymer, and preferably less than 1% of any contaminant polymer.

An additional embodiment of the invention provides a process for preparation of poly(ethylene glycol) monomethyl ether (MPEG) from poly(ethylene glycol) (PEG). The method comprises heating PEG with toluene, pyridine, and $SOCl_2$ to form a polymeric mixture; reacting the polymeric mixture with methanol, KBr and KOH to form a mixture containing MPEG; reacting the mixture containing MPEG with a derivatizing molecule Q to form a mixture containing a derivatized polymer MPEG-Q; said derivatizing molecule comprising (i) 2 or 3 ionizable groups and a group available for covalent bonding with a terminal hydroxy group of MPEG; or (ii) 3 or 4 ionizable groups, at least one of the ionizable groups being available for covalent bonding with a terminal hydroxy group of MPEG; subjecting the mixture containing derivatized polymer MPEG-Q to ion exchange; collecting a fraction containing the derivatized polymer MPEG-Q; and removing the derivatizing molecule from the derivatized polymer MPEG-Q to form poly(ethylene glycol) monomethyl ether. The product formed as a result of this process, a purified MPEG, is also considered an embodiment of the invention. The MPEG product may comprise less than 2% contaminant polymer, and preferably less than 1% of any contaminant polymer.

Advantageously, the invention allows formation of an ester or other easily reversible bond between a PEG hydroxyl and another species, in reaction typically referred to herein as an acylation reaction.

As a more specific example of the technology, the invention allows the separation, purification and analysis of simple linear polymers having two terminal groups of the same or similar chemical reactivity from linear polymers having no or only one chemically reactive end.

Further, embodiments of this invention can achieve a highly efficient purification of MPEG from PEG by chromatographic means that these same means can be applied to yield highly efficient and accurate analytical separations for the analysis of PEGs, MPEG and the derivatives of these and like polymers. This permits methods of analysis of polymeric materials.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures. Unless otherwise noted, all HPLC chromatograms were produced using an evaporative light scattering detector (ELSD).

DETAILED DESCRIPTION

Figure 1:
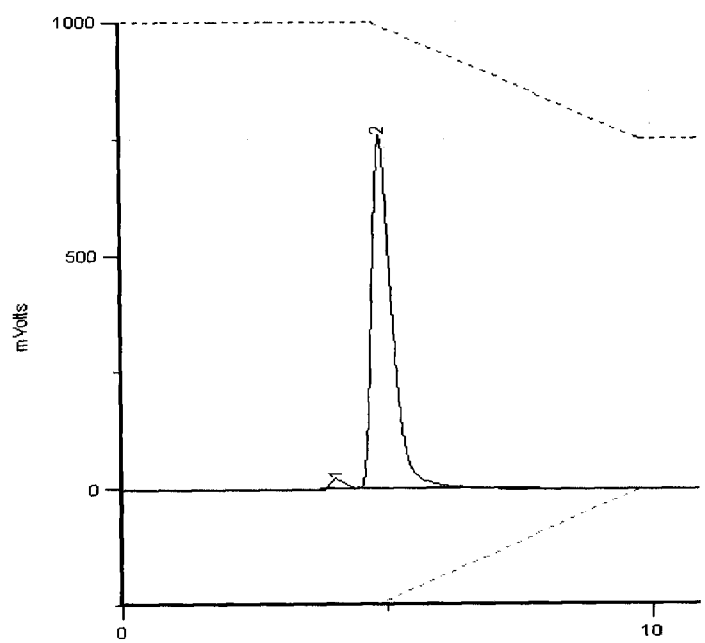
FIG. 1 is a chromatogram of MPEG 10,000 Da phthalic acid ester according to Example 1.

The invention relates to a method of separating or purifying water soluble polymers, allowing separation or purification of these polymers from contaminants or from impurities arising in their production. The invention encompasses the preparation of polymer derivatives in a way that permits and facilitates the separation, purification, and/or analysis of such polymers after derivatization. The derivatization may be reversible, allowing purified polymers to be obtained. The purification and analysis of such water soluble polymers as poly(ethylene glycol) hetero bi-functional derivatives is accomplished using a specific class of derivatizing molecules having more than one ionizable group. The invention provides advantages over prior art methods of purification and analysis. Preferred derivatives possess more than one ionizable group, that is: a group capable of possessing either more than one anionic charge or more than one cationic charge. These derivatives allow for chromatographic ion exchange separation of polymer species having different numbers of derivatizing molecules thereon into pure fractions. For example, an ion exchange column may be used to separate derivatives having different numbers of derivatizing molecules thereon, due to distinct retention times on a column under certain elution conditions.

The invention provides a process for purification of a water soluble polymer of interest from an initial mixture of polymers, wherein the polymer of interest contains a different number of reactive terminal groups than other polymers in the mixture. The process comprising reacting the initial mixture of polymers with a derivatizing molecule to form a reacted polymer mixture, said derivatizing molecule comprising (i) 2 or 3 ionizable groups and a group available for covalent bonding with a reactive terminal group of polymers in the initial mixture; or (ii) 3 or 4 ionizable groups, at least one of the ionizable groups being available for covalent bonding with a reactive terminal group of polymers in the initial mixture; subjecting the reacted polymer mixture to ion exchange; and collecting a fraction containing the polymer of interest.

The group available for covalent bonding may be an ionizable group, but need not necessarily be considered as an ionizable group per se before the derivatizing molecule is reacted with the polymer mixture. In an embodiment wherein the covalent bond between the derivatizing molecule and the reactive terminal of a polymer is an ester bond, such a bond may be formed between a carboxylic acid anhydride group of the derivatizing molecule and an alcohol group on the polymer. The group available for covalent bonding may be, for example, a halide, one of the acid groups forming an anhydride, an acid, an ester, or an ionizable group that is the same as or different from other ionizable groups on the molecule. In an exemplary embodiment, a derivatizing molecule may have three or four ionizing groups which may be the same or different from one another. One of these ionizing groups may be used as the group available for covalent bonding with a reactive terminal of a polymer. The derivatizing molecule may thus be described as one comprising 2 or 3 ionizable groups, and an additional group for forming the covalent bond. Such terminology is used when the group for forming the covalent bond may not fall within a narrow concept of the meaning of the term "ionizable group". Alternatively the derivatizing molecule can be described as one comprising 3 or 4 ionizable groups, one of which is utilized or consumed in the formation of the covalent bond.

An optional additional step may be included to remove the derivatizing molecule from the polymer of interest, after the step of collecting. Additionally, the optional step of collecting a fraction containing a contaminant polymer other than the polymer of interest may be included in the process. The derivatizing molecule is removed from the contaminant polymer after collection.

The invention also provides a process for separating one or more contaminant polymer from a polymer of interest, wherein the polymer of interest comprises n reactive terminal groups and the contaminant polymer comprises m reactive terminal groups, wherein n and m are whole numbers and n≠m. The term "whole numbers" as used herein is understood to encompass the number zero. The process comprises acylating the reactive terminal groups with a derivatizing molecule possessing 2 or 3 ionizable groups, forming a reversible bond; and separating the contaminant polymer from the polymer of interest using ion exchange chromatography.

The reactive terminal groups may be any reactive group available to form bonds with the group on the derivatizing molecule available for forming covalent bonds. Exemplary reactive terminal groups include hydroxyl groups, sulfhydryl or mercapto groups, aldehyde groups, halide groups, carboxylate groups or amino groups. Sulfhydryl groups can form thioester or thioether bonds to the derivatizing molecule. Aldehydes can be reductively aminated by reaction with amines and a reducing agent. Halides can be displaced by nucleophilic centers of the derivatizing molecule forming a thioether, for example, with a mercaptan containing derivatizing molecule. A carboxylate can be reacted with an alcohol or an amine group on the derivatizing molecule to form an ester or amide bond, respectively. Amino groups may form amide bonds when covalently bound with a derivatizing molecule. Some of these reactive groups will not be readily removable and thus will be primarily useful for removal of undesired polymers having reactive terminal end groups or for analysis of mixtures for polymer composition, but less useful in preparative processes when removal of the derivatizing molecule is desirable.

In the process, one or more contaminant polymer may be present, for example, 2 or more contaminants. In each case, m can be selected independently for each contaminant polymer. Exemplary values of n and m are: when n=0 and m=1, 2 or ≧3; when n=1 and m=0, 2, or ≧3; and when n=2 and m=0, 1, or ≧3.

The step of removing the derivatizing molecule from the polymer of interest or the contaminant polymer after the step of separating can be employed according to the process.

The ion exchange used in the process may comprise ion exchange chromatography or ion exchange membrane separation. When ion exchange chromatography is employed, the process may be conducted on a single column. Ion exchange chromatography may be carried out isocratically, using a pH gradient, or using an ionic strength gradient to elute the desired fractions. The gradient may be either a continuous gradient or, more preferably, a step gradient in which a distinct change of ionic strength or pH is undertaken as is common in the art of ion exchange separations.

In an exemplary embodiment, the polymer of interest may have one reactive terminal group and other polymers in the mixture may have zero or two reactive terminal groups. The polymer of interest may be linear or branched. Preferably, when the polymer of interest has reactive groups, the reactive groups are found only at the terminal polymer ends, and not at various internal sites along the length of the polymer. A specific polymer of interest may be MPEG, and in certain examples, the initial mixture of polymers to be purified may comprise a mixture of MPEG and PEG. An exemplary mixture may be one comprising less than 10% PEG, and MPEG as the remainder of the polymers in the mixture.

The initial mixture of polymers may include MPEG and PEG having an average size of about 100,000 Da or less. Further, the initial mixture of polymers may comprise MPEG and PEG, each having an average size of about 9,000 Da or greater. Further, the initial mixture of polymers may comprise MPEG and PEG, with the PEG having a molecular weight of about twice the molecular weight of the MPEG present in the mixture.

Prior to the step of reacting the initial mixture of polymers, the process may involve the step of preparing MPEG by ethylene oxide polymerization thereby forming a mixture of polymers containing MPEG and PEG.

The derivatizing molecule may comprise two or three anionic ionizable groups, or two or three cationic ionizable groups in addition to a group having a site available for covalent bonding, which may itself be an ionizable group. In the embodiment where the group having a site available for covalent bonding can be categorized as an ionizable group, it may be either cationic or anionic, regardless of the nature of other ionizable groups present. The group having the site available for covalent bonding is utilized when reacted with the reactive terminal groups of the polymer, and thus, in the resulting derivatized polymer, the covalent bond is present. Thus, after reacting with the polymer, this covalent bonding site (which fell within the category of an ionizable group on the derivatizing molecule) may no longer be available as an ionizable group. An anionic ionizable group utilized in the covalent bond formed in the derivatization process is no longer ionizable after reaction. A cationic ionizable group utilized in the covalent bond formed in the derivatization process may still be available as an ionizable group when reaction is with an aldehyde or a —$CH_2$—X terminal group wherein X is a leaving group capable of nucleophilic displacement.

By way of illustration, an exemplary derivatizing molecule may have three ionizable groups, two of which are carboxylate groups and one of which is a sulfonic acid group. One of the two carboxylate groups may be the group having a site available for covalent bonding to the polymer, thereby resulting in a polymer covalently bound to a molecule having two ionizable groups thereon, one a carboxylate group and the other a sulfonic acid group. Another illustrative example of a possible derivatizing molecule for use in the process would be one having 4 ionizable groups, all of which are carboxylate groups, such as benzene tetracarboxylic acid or its corresponding di-anhydride form. In reacting with the reactive terminal groups of polymers within a polymer mixture, any one of the available ionizable groups may be utilized in the covalent bond, resulting in a derivatized polymer having three remaining carboxylate groups at the reacted terminal ends. Yet a further example is a derivatizing molecule comprising 2 ionizable groups and one group with a site available for covalent bonding, such as a halide, which may not be considered to fall within a narrow definition of an ionizable group. Once the site bearing the halide is reacted with the polymer to form a covalent bond, the resulting derivatized polymer comprises 2 ionizable groups at each reacted terminal end. On the basis of these examples, it should be clear to a person of skill in the art that the choice of derivatizing molecule may have 2, 3, or 4 ionizable groups, provided that after the reaction to form a covalent bond, the resulting derivatized terminal ends of the polymer comprises 2 or 3 ionizable groups.

The capacity of a derivatizing molecule to ionize can be evaluated when the derivatizing molecule is present in aqueous media, and under appropriate pH conditions. For example, many molecules typically considered capable of ionization under typical reaction conditions may not show such characteristics at pH extremes, or when present in non-aqueous media. A person skilled in the art would understand an ionizable group to be one capable of ionizing under such typical conditions, even if such ability can be hindered under atypical reaction conditions. Under conditions conductive to ion exchange, the ionizable groups of the derivatized polymers may not be fully ionized, and may result in a net charge that is not a whole number. For example, under certain conditions, a group having 2 ionizable groups may be in a state of equilibrium where 20% of the molecules are not in and ionized state, while 80% of the molecules are in an ionized state. However, such a molecule would still be considered to have 2 ionizable groups, regardless of the net charge under particular conditions. The number of ionizable groups refers to the number of groups available for ionization, not the net charge of a particular molecule under given conditions, as would readily be understood by one of skill in the art. Further, the ionizability of a group is evaluated under aqueous conditions, as opposed to non-aqueous conditions. This means that ionizable groups originally present as organic cyclic carboxylic acid anhydrides, for example, would be considered eligible ionizable groups, regardless of the ionic status under non-aqueous conditions or prior to reaction. Any unreacted anhydride functions would be converted in water to the corresponding dicarboxylic acid form and contribute two ionizable groups. In general, the number of ionizable groups that will remain at each derivatized termini of a polymer once a covalent bond is formed is 2 or 3 and practically will be less than 5.

A typical anionic derivatizing molecule is one comprising 2 or 3 ionizable anionic groups, which are independently selected from the group consisting of carboxylate, phosphate, phosphonate, borate, sulfonate, and sulfate groups when present in aqueous media. Thus, the ionizable groups present on any given derivatizing molecule need not be identical to each other. An exemplary derivatizing molecule is a di-anion, for example, a benzene derivative. The derivatizing molecule may be an acid anhydride, a cyclic anhydride, an intramolecular anhydride, or an aromatic intramolecular anhydride. Specific derivatizing molecules include 1,2,4-benzene tricarboxylic acid anhydride, 1,2,4,5-benzene tetracaboxylic acid dianhydride, 1,2,3,4-cyclobutane tetracarboxylic acid dianhydride, and 2,2',3,3'-dicarboxybenzophenone dianhydride. The derivatizing molecule may be referred to herein for convenience as "Q". An exemplary polymer having a derivatizing molecule covalently bound thereto may be referred to herein as MPEG-Q or EtO-PEG-Q, for convenience.

A typical cationic derivatizing molecule is one comprising 2 or 3 ionizable cationic groups independently selected from the group consisting of amine, aromatic amine, and heterocyclic nitrogen containing groups, when present in aqueous media.

A specific exemplary process may be one in which the polymer of interest is a poly(ethylene glycol) polymer having one reactive terminal group. The initial mixture of polymers may comprise a poly(ethylene glycol) polymer having two reactive terminal groups admixed with the polymer of interest. The step of reacting may comprise acylation with the derivatizing molecule, and ion exchange chromatography is employed to elute a fraction containing the polymer of interest at a distinct retention time or at a specific ionic strength of eluant A further specific exemplary process may be one in which the polymer of interest is mono alkyl ether end capped poly (ethylene glycol); the contaminant polymer comprises one or both of poly(ethylene glycol) or bis alkyl ether end capped poly(ethylene glycol); and the alkyl ether end cap is unreactive in an acylation reaction with simple organic anhydrides at temperatures under 130° C. For example, the polymer of interest may be methoxy ether end capped poly(ethylene glycol).

In an exemplary process, the polymer of interest, after separation from the contaminant polymer, may be greater than 98% pure. In an exemplary embodiment of the process the polymer of interest, after separation from the contaminant polymer, may be greater than 99% pure.

The invention also provides mono ether end capped poly (ethylene glycol) which has been separated according to any of the processes described herein and having less than 1% poly(ethylene glycol) content. The ether end cap can be a lower alkyl (C1 to C6 alkyl) or aryl or benzyl or substituted benzyl or triphenylmethy ether group.

A typical polymer mixture that falls within the scope of the invention may comprise poly(ethylene glycol) polymers having the general formulae: $R_1$—O-PEG-O—$R_1$ and $R_1$—O-PEG-O—$R_2$ wherein —$R_1$ comprises a di-anion, a tri-anion, a di-cation or a tri-cation; and —$R_2$ is a straight-chain alkyl group containing 1 to 4 carbon atoms, or a benzyl or triphenylmethyl (trityl) group. For example, —$R_1$ may comprise a di-anion and —$R_2$ can be methyl. In such a mixture, less than 2% $R_1$—O-PEG-O—$R_1$ may be present.

The invention also provides a method for analysis of an initial mixture of two or more water soluble polymers, wherein each polymer has a different number of reactive terminal groups. The method comprises the steps of reacting the initial mixture with a derivatizing molecule to form a reacted polymer mixture; said derivatizing molecule comprising (i) 2 or 3 ionizable groups and a group available for covalent bonding with the reactive terminal groups; (ii) 3 or 4 ionizable groups, at least one of the ionizable groups being available for covalent bonding with the reactive terminal groups; or (iii) 2, 3 or 4 amine groups, one of the amine groups being available for covalent bonding with a reactive terminal group consisting of an aldehyde or —CH$_2$—X wherein X is a halide, sulfonic acid ester or other leaving group; subjecting the reacted polymer mixture to ion exchange; and evaluating polymer content of ion exchange fractions.

This analytical embodiment does not require collection of separated reacted polymer mixture. It also does not require the derivatizing molecule(s) to be capable of being removed to regenerate the original polymer(s), thus certain additional derivatizing molecules produce reacted polymer mixtures sufficient for analysis, although certain derivatizing molecules may not be removable. For example, when the derivatizing molecule is an amine containing molecule and this is coupled to the reactive terminal group of a polymer using reductive amination or nucelophilic displacement of a leaving group on the polymer, the site of attachment will be a secondary amine and will still represent an ionizable group even after the covalent bond to the polymer is formed and thus, only 2 ionizable amine groups would need to be present in the derivatizing molecule to form a polymer product with 2 ionizable groups. Should an amine be used to form an amide linkage to a polymer, such a linkage would be neutral and the amine would need to be one of three or four ionizable groups present such as in case ii above.

Further, in such analytical embodiments, the step of evaluating polymer content is used to demonstrate that the initial mixture contains predominantly one polymer of interest and a negligible amount of contaminant polymers. Evaluating polymer content may be used to determine content, either qualitatively or quantitatively, of a reactive polymer in such applications where only a specific polymer possessing a particular reactive termini can be converted to a derivatized polymer. Additionally, the step of evaluating polymer content could be used to determine presence or amount of any polymer in the mixture that can react more than once with the derivatizing molecule. The method may additionally comprise measuring the amount of a reactive product formed from a PEG species present in a reactive MPEG polymer or mixture.

An additional embodiment of the invention provides a process for preparation of poly(ethylene glycol) monomethyl ether (MPEG) or poly(ethylene glycol) monoethyl ether (EtO-PEG) from poly(ethylene glycol) (PEG). The method comprises heating PEG with toluene, pyridine, and SOCl$_2$ to form a polymeric mixture; reacting the polymeric mixture with methanol (if MPEG is desired) or ethanol (if EtO-PEG is desired), along with KBr and KOH to form a mixture containing MPEG (or EtO-PEG); then reacting this mixture containing MPEG (or EtO-PEG) with a derivatizing molecule Q to form a mixture containing a derivatized polymer MPEG-Q (or EtO-PEG-Q); said derivatizing molecule comprising (i) 2 or 3 ionizable groups and a group available for covalent bonding with a terminal hydroxy group of MPEG (or EtO-PEG); or (ii) 3 or 4 ionizable groups, at least one of the ionizable groups being available for covalent bonding with a terminal hydroxy group of MPEG (or EtO-PEG); subjecting the mixture containing derivatized polymer MPEG-Q (or EtO-PEG-Q) to ion exchange; collecting a fraction containing the derivatized polymer MPEG-Q (or EtO-PEG-Q); and removing the derivatizing molecule from the derivatized polymer MPEG-Q (or EtO-PEG) to form poly(ethylene glycol) monomethyl ether. The product formed as a result of this process, a purified MPEG, is also considered an embodiment of the invention. The MPEG (or EtO-PEG) product may comprise less than 2% contaminant polymer, and preferably less than 1% of any contaminant polymer.

Variations may be made in the above-noted process, as would be understood by those skilled in the art. For example, other solvents may be used in place of the exemplary solvents pyridine and toluene. 1,2,4-benzenetricarboxylic anhydride is an exemplary derivatizing molecule which may be used in such a process, however, alternative derivatizing molecules may be used. Use of methanol and ethanol are exemplified, but other alcohols may be used. A symmetrical PEG derivative may be employed, without regard to how it was made (or it could be prepared from PEG) wherein the ends have become leaving groups. For example, halides such as Cl, Br or I may be employed. Sulfonic acid esters of PEG such as: tosy and mesyl p-tolulene sulfonic acid PEG esters, methyl sulfonic acid PEG esters or other leaving groups may be used. The process involves a reaction with a lower alkyl alcohol such as methanol (for MPEG) and a base strong enough to promote the displacement of the leaving group with the methoxide or alkoxide form of the alcohol. It is desirable to obtain about 50% displacement, either directly competing or, in a further step, reacting with hydroxide ion to remove the remaining leaving group and replace with OH, this can be done with KOH where there will be some competing reaction with OH.

For example, PEG may be converted to a Bis leaving group-PEG, and subsequently, OR and OH anions sequentially or in competition make a mixture of RO-PEG-OR, RO-PEG-OH and HO-PEG-OH. At this point, RO-PEG-OH may be separated from the mixture according to the method of the invention, using the subsequent steps of reacting the mixture with a derivatizing molecule, and subjecting the mixture to ion exchange.

Embodiments of the invention allow the production of poly(ethylene glycol) monomethyl ether (MPEG) essentially free of any poly(ethylene glycol) (PEG). Analytical results for such polymers are also significantly enhanced and the formation of these derivatives allows certain analyses that are difficult to carry out by other means to be conducted with relative ease.

The invention incorporates an ion exchange process to purify water soluble neutral polymers that are either linear or branched in nature with one or more reactive end groups. The polymers to be purified have the property that only the reactive terminal end groups of the polymer chain or chains are readily capable of chemical modification through reactions such as alkylation, acylation, amination, or oxidation. Advantageously, such chemical modification occurs selectively at the terminal ends of the polymer chains without degrading the polymer chain(s).

The polymer of interest can be purified from an impure mixture of polymer components. Impurities in the mixture may arise from, for example, the initial synthesis of the polymer, the incomplete chemical modification of the polymer, or from undesired side reactions which may occur in synthesis or modification.

The invention allows for separation of polymer of interest from impurities when there are differences in the number and/or the chemical nature of reactive terminal end groups present.

The mixture containing the polymer to be purified or separated can be reacted to form a product at greater than 90% conversion of polymer terminal end groups. It is not necessary to have complete derivatization to yield a product that is pure or has been significantly purified. The reactive terminal end of the polymer mixture so formed are converted into a group capable of possessing more then one ionic charge, or having more than one ionizable group, and preferably having 2 or 3, ionizable groups.

Separation of the mixture of products so formed into fractions can then be conducted using an ion exchange process.

One or more polymer of interest may be recovered from the fractions obtained by ion exchange at a level of at least 98% purity with respect to the number of reactive terminal groups present. A level of 99% purity may be accomplished (that is to say having 1% or less contaminant polymer content). Advantageously, the ion exchange separation of the mixture can be done using an ion exchange column, or can be conducted using an ion exchange membrane.

According to embodiments of the invention, the derivatization of the end groups with a derivatizing molecule having more than one ionizable group, forming end groups capable of possessing more than one ionic charge, can be reversed to recover the original polymer.

According to certain embodiments of the invention, the process allows separation of a mixture by ion exchange chromatography with the end result that over 40% of the desired product present in the mixture is obtained at a level of at least 98% purity. In an exemplary embodiment of the invention, over 50% of the desired product present in the mixture is obtained at a level of at least 98% purity.

The process allows purification of a water soluble polymer of interest that is either a minor component of a polymer mixture, or which is a predominant component of a polymer mixture. Provided the polymer of interest has 0, 1 or 2 reactive terminal ends, it can be separated from other polymeric components in the mix having a different number of reactive terminal ends, regardless of the prevalence of the polymer of interest within the mixture.

According to an embodiment of the invention, when the polymer of interest is the most prevalent polymer and has no reactive terminal ends, it can be purified by ion exchange, by retaining derivatized polymers (possessing reactive terminal ends) while the polymer of interest is eluted.

According to a further embodiment of the invention, when the polymer of interest has one reactive terminal end, upon derivatizing the polymer mixture according to the invention, the polymer of interest can be purified using ion exchange by elution of contaminant polymers having no reactive terminal ends. Further, by using an eluant that selectively elutes the polymer of interest but not other polymers having more than one reactive terminal end, the polymer of interest can be eluted in a distinct fraction.

According to an embodiment of the invention in which ionizable groups are negatively charged, polymeric products formed by derivatization of the reactive end groups have more than one negative or anionic charge per reactive polymer terminal group. This permits ion exchange separation. For example, the more than one negative or anionic charge on the resulting polymer derivative may be present as carboxylate, phosphate, phosphonate, borate, sulfonate, or sulfate substituents, or mixtures thereof.

According to an embodiment of the invention in which ionizable groups are positively charged, polymeric products formed by derivatization of the reactive end groups have more than one positive or cationic charge per reactive polymer terminal group. The charge may be present as amine, aromatic amine, or heterocyclic nitrogen containing group capable of bearing a positive charge in aqueous solution, or mixtures of these.

The invention provides a process for purifying poly(ethylene glycol) polymers having one reactive group capable of reversible acylation from similar and related poly(ethylene glycol) polymers having either zero or more than one reactive groups. The reactive group may be acylated with a modifying molecule that will yield a product with more than one ionizable group. The resultant polymer mixture is chromatographically purified by ion exchange chromatography under conditions that permit components having more than one charge for each modifying molecule attached to be separated from other molecules in the mixture having no charge or molecules with more reactive groups and thus more multiply charged molecules attached.

The fraction of the mixture containing polymers having no modifying molecule attached is not bound by the ion exchange material, and is readily eluted.

The fraction containing a polymer with only a single modifying molecule attached is first bound and then recovered from an ion exchange column in essentially pure form, and the modifying molecule can then be removed to yield a pure polymer with only a single reactive group. In instances where there is an absence of polymers having no modifying molecules attached, the initial conditions can be adjusted so the polymer with a single modifying molecule attached is not bound but all other polymers with more than a single modifying molecule attached are bound.

Optionally, additional bound components may be obtained in essentially pure form based on the number of reactive groups present in each species. These may also have the modifying molecule removed to give fractions having the same number of reactive groups.

The invention also provides a process for producing pure mono alkyl ether end caped poly(ethylene glycol) (RO-PEG-OH) wherein a mixture of mono alkyl ether end caped poly(ethylene glycol) (RO-PEG-OH), PEG with no end substitution (HO-PEG-OH) and PEG materials with no available hydroxyl groups, such as the bis alkyl ether end capped poly(ethylene glycol) (RO-PEG-OR or more generally R-PEG-R) wherein alkyl group "R" has no reactive group capable of acylation by simple organic anhydrides at temperatures under 130° C. In this embodiment, the hydroxyl groups and any other readily alkylated groups in the mixture are acylated with a modifying molecule that will yield a product with more than one ionizable group at each substitution point. The fraction having no modifying molecule attached is not bound by the ion exchange material. The resultant polyethylene glycol polymer product mixture is chromatographically purified by ion exchange chromatography under conditions where the products will have more than one charge for each of the modifying molecules attached. The fraction containing the RO-PEG-OH polymer product with only a single modifying molecule attached is recovered, and the modifying molecule is removed to yield a pure RO-PEG-OH.

The invention further provides a process for producing pure methoxy ether end caped poly(ethylene glycol) (MPEG) from a mixture containing MPEG, poly(ethylene glycol) (PEG) with no end substitution, and/or PEG materials with no available hydroxyl groups such as the bis alkyl ether end capped poly(ethylene glycol) (RO-PEG-OR) or more generally R-PEG-R wherein R has no reactive groups capable of acylation by simple organic anhydrides at temperatures under 130° C. Such a mixture is typical of conventional synthesis of MPEG from ethylene oxide, in which PEG is commonly found at levels of 1 to 20% as an impurity. In this instance, hydroxyl groups are acylated with a modifying molecule that will yield a product with more than one ionizable group at each substitution point. The resultant MPEG polymer in the mixture is chromatographically purified from the mixture by ion exchange chromatography under conditions where the products will have more than one charge for each of the modifying molecules attached. Upon recovery of the fraction containing the MPEG polymer with only a single modifying molecule attached, the modifying molecule may then be removed to yield a pure MPEG with less than 1% PEG present.

Optionally, additional fractions may be obtained from the mixture in essentially pure form based on the number of reactive groups present in each polymer species. The modifying molecule can be removed from the fractions obtained to give pure fractions having the same number of reactive groups. Materials with no available hydroxyl group are not bound to the ion exchange chromatography, and can be eluted readily in a distinct fraction.

The MPEG product with a multiply charged modifying molecule bound thereto becomes bound to the ion exchange chromatography medium to which it is applied, and may then be eluted from the medium. Elution may occur by any means acceptable to those skilled in the art of ion exchange chromatography such as a change in pH or ionic strength. Typically the desired fraction is then eluted by raising the salt concentration of the chromatography elutant.

When bound to the ion exchange chromatography media, the MPEG product with the modifying molecule can be eluted by changing the pH of the chromatography elutant, by changing the ionic strength of the chromatography elutant, or by a combination of these.

The invention further relates to a monoalkylether end capped poly(ethylene glycol) or MPEG with less than 1% total poly(ethylene glycol) or PEG content, which may be formed using the method of the invention. The total PEG content may include both PEG of molecular weight larger than the average molecular weight of the MPEG and PEG molecules with similar and lower molecular weights. The MPEG may be originally produced using ethylene oxide polymerization, or any method as would be known to a person of skill in the art.

A pure branched poly(ethylene glycol) polymeric material with only a single reactive site can be produced, in which less than 1% of the branched poly(ethylene glycol) segments have a hydroxyl group. The remaining branched poly(ethylene glycol) segments—may have substantially complete alkyl ether end-capping.

A pure MPEG product may be produced from a MPEG wherein the product has been purified by removal of all unreacted MPEG. This can be done by first reacting the impure derivative with a modifying agent capable of reacting with MPEG terminal hydroxyl groups. Such a modifying agent can also produce a new derivative of the MPEG material, such as one capable of having more than one negative or positive charge under conditions suitable for ion exchange chromatography.

A method of analysis of linear or branched water soluble polymers containing one or more alkyl ether end capped poly(ethylene glycol) polymer chains can be conducted according to the invention. In this method, derivatives are formed using reagents that possess more than one positive charge for each molecule attached to the polymer material. Subsequently, the resultant products can be separated by ion exchange chromatography.

Exemplary derivatives may be formed from polymer hydroxyl groups, from polymer amine groups, from polymer aldehyde or ketone groups, or from polymer end groups capable of reacting with a simple mercaptan such as cysteine or mercaptoethanol.

According to one aspect of the invention there is provided an improved method of analysis of the PEG content of MPEG wherein the hydroxyl groups of the mixture of PEG and MPEG are first reacted and converted to derivatives capable of possessing more than one charge for each molecule attached. The resulting product is analyzed by ion exchange chromatography. The derivative formed may have negative (or anionic) charge groups, or alternatively, may have positive (cationic) charge groups. For example, the derivative may be formed by reacting the polymer with an acid anhydride, such as an intramolecular anhydride, or an aromatic intramolecular anhydride. Specific anhydrides which may be used are 1,2,4 benzene tricarboxylic acid anhydride; 1,2,4,5 benzene tetracarboxylic acid dianhydride; 1,2,3,4 cyclobutane tetracarboxylic acid dianhydride; or 2,2',3,3' dicarboxybenzophenone dianhydride.

In the method of the invention, ion exchange chromatography can be carried out isocratically, by using a pH gradient, or by using an ionic strength gradient. The gradient can be accomplished with a series of discreet steps or in a continuously variable manner.

The methodology of the invention is preferably used for purification of water soluble polymers with only reactive end groups, as opposed to those polymers having reactive groups within the chain. The invention is particularly useful when the polymer is PEG or PEG mono alkyl ethers Branched and linear water soluble polymers may be used, such as branched PEGs and MPEGs. Exemplary branched materials are those in which the site of branching, when incompletely reacted and therefore not fully branched, can be separated from fully branched materials.

The invention may be particularly useful for polymers over 9,000 Da, which have been heretofore viewed as inappropriate candidates for chromatographic separation.

The invention is capable of scale-up to high capacity and high yield procedures, in large scale batches greater than 10 kg, and further in batches greater than 20 kg. When large batch purification is used the isolated individual component yield can be greater than 40% pure component.

The polymer may first be converted to an intermediate form and a selected impurity may be removed which may then become the unreacted polymer starting material. In this way, a very high yield can be achieved on the basis of the fraction of starting material utilized. Further, if upon conducting the reactive process, the target reacts and is purified, reaction byproducts or earlier intermediates in the synthesis which are non-reactive may be removed by virtue of not binding to an ion exchange column.

Nearly pure material made from impure starting material can be separated into non-reactive polymer, mono-reactive end capped polymer and fully reactive material. In a specific example of this, pure MPEG can be obtained with PEG removed. Both straight-chain and branched PEG/MPEG derivatives may be separated in this way. A specific example of this may be one in which purified MPEG is obtained in a purified form based on purification of the product of a poly(ethylene glycol) based synthesis in which over 2% PEG was originally present. MPEG can be obtained in essentially pure form from a PEG-based synthesis having as much as 15% PEG contaminant present.

Purified MPEG having more than one charge introduced at each reactive termini is formed according to the invention.

Purification or re-purification of MPEG or other polymers after conversion to a new functional polymer by via end group modification may be conducted according to the invention. In such an instance, unreacted polymer may be considered a recoverable impurity that reacts with derivatization materials to render it removable. In reactions wherein more than one step has been carried out to achieve a product, intermediates can be derivatized and separated from non-reactive byproducts of the synthetic route.

The invention further relates to the use of multi-charge derivatives for separation for analysis of terminally reactive polymer materials, including both branched and linear polymer materials. Materials successfully formed in a branching process can be separated or analysed to determine branch failure analysis. Further, in processes aimed at adding reactive groups, analysis of the success of the reaction can be done according to the invention.

Polymer mixtures may be analysed, such as PEG present in MPEG. Both low and high molecular weight PEG in MPEG can be analysed. Functional end group analysis by ion exchange may also be conducted according to the invention. For many analytical purposes, the chemistry of derivatization does not need to be reversible. However, there may be advantageous reasons why the derivatization reaction can be reversible, for example, so that impurities may be removed and added again to a subsequent reaction as starting materials. For reactions in which further modification of the original polymer to a new product or intermediate is desirable, if the material present as an impurity is the reactive species and the desired product does not react, the derivatization does not need to be reversible.

The use of multi-charged derivatives in combination with ion exchange allows clean purification of unreacted product. Bulk synthetic processes may be used. Advantageously, a high yield may be achieved. A further advantage is that purification may be done on a simple ion-exchange column, or alternatively, using an ion exchange membrane.

Purification of a 20,000 Da MPEG contaminated by both 40,000 Da PEG and low molecular weight PEG arising from the production via an ethylene oxide polymerization can be conducted according to the following exemplary steps.

a. Derivatization to make the di-anion MPEG and tetra anion PEG in high yield and high conversion.
 b. Analysis of the PEG in the MPEG above both before and after purification as the multicharged anion derivative, resulting in either (i) a diacid derivative or (ii) a triacid derivative.
 c. Ion exchange purification of the materials.
 d. Removal of the reversible derivative group and recovery of the pure MPEG.

After the purification is conducted, analysis of the unretained PEG fraction can be conducted to demonstrate that there is a neutral or unreactive impurity that is also removed.

Similar purifications having the steps listed above can be done with a different molecular weight MPEG, and/or with a different derivative molecule used.

Similar purifications having the steps listed above can be done with other water soluble polymers bearing terminal alcohol or amine groups such as poly(vinyl alcohol) and end capped monofunctional derivatives of such polymers.

Conversion of pure MPEG into a different MPEG alcohol derivative can be conducted according to the invention, followed by purification of this product from neutral precursors. The invention may also be used for purification of a branched PEG derivative. Analysis of MPEG aldehyde by conversion to a poly cation, followed by IEX chromatography can be conducted according to the invention.

Exemplary polymers which can be purified according to the invention include di- and tri-cationic derivatives of MPEG aldehyde and/or MPEG propionaldehyde, or di-anionic derivatives of MPEG maleimide or MPEG iodoacetamide.

Advantageously, aspects of the invention allow the production of pure MPEG from MPEG containing PEG.

Advantageously, embodiments of the invention involve linear PEG materials above about 9,000 Da The process may be used to purify an intermediate in a multistep synthesis, or to achieve a purified end-product.

The invention relates to compounds and means to produce purified water soluble polymers. Compositions of matter that facilitate the purification, methods of purification and methods of analysis of the water soluble polymers are all disclosed. The invention is particularly suited to the separation of water soluble polymers having a chemically reactive end capable of reversible chemical modification from related polymers having two or more such reactive terminal end or from polymers having no such reactive end. By way of further describing the invention, it can be illustrated by way of example by describing the purification of polymers of poly (ethylene glycol). In particular, there exists a need for highly purified mono-methoxy ether of poly(ethylene glycol) where one end of the polymer is rendered essentially non-reactive and the other end posses a hydroxyl group that can be converted into a variety of reactive functional groups by one skilled in the art of such polymer chemical modification. While there can be additional stages in the synthesis of such activated MPEG derivatives wherein the invention can be utilized to purify an intermediate reaction product of a multistep synthesis, it is in the large scale purification of the basic MPEG material that the invention has its greatest utility. Without a pure MPEG starting material, subsequent chemical reactions can not be expected to produce pure reaction products and can only yield increasingly complicated mixtures of products.

As is commonly know, the production of alkyl end-capped poly(ethylene glycol)s such as MPEG by the anionic polymerization of ethylene oxide via initiation with a methyl end capped initiator routinely produces poly(ethylene glycol) polymers as an impurity. Although some manufacturers produce MPEG with low PEG levels, some of the PEG impurity is always present. PEG content can range as high as 10-15%, or in some cases, even higher. The PEG in MPEG arises from the presence of trace amounts of water contamination during the base catalyzed polymerization of ethylene oxide using methyl end-capped initiator. Due to a lower concentration of initiator in the preparation of high molecular weight PEGs, e.g., exceeding 20,000 Da or so, even low level water contamination and hence diol formation can present a serious problem. For high molecular weight MPEG, diol contamination can reach or even exceed 30%. Further, because the diol chain can grow at each end, the contaminating diol typically has a higher average molecular weight than the desired MPEG.

The production of purified MPEG by reduction of these PEG polymer contaminants has not heretofore been achieved on a commercial scale. The invention described herein has allowed the production of MPEG material comparable in quality to the best commercial grade material available.

The separation of ionic forms of PEG polymers in the molecular weight range of 10,000 to 30,000 and higher Daltons is difficult, as has been reported. While analytical separation can often be achieved on microgram samples to allow, for example, the measurement of the PEG content of a MPEG sample, the materials are marginally separated at best. Shallow gradient elution is used to facilitate the analytical separations. Attempts to carry out preparative separations on multi gram or kilogram levels have been unsuccessful.

The purification of MPEG contaminated with PEG in its manufacture is further made difficult by the fact that the PEG present is typically about twice the molecular weight as the desired MPEG. As the molecular weight of these polymers increases, their binding to chromatographic media decreases. Separations that are well resolved such as the separation of 10,000 Da PEG from a 5,000 Da MPEG become very difficult when the size increases to 40,000 PEG from a 20,000 MPEG.

Since many properties of ionic materials are related to their charge to mass ratio, it is not surprising that a) smaller molecular weight ionic derivatives of MPEG bind more strongly to an ion exchange matrix than larger molecular weight derivatives and the b) the PEG derivatives formed in impure MPEG are difficult to separate since they are twice the mass as well as having twice the charge after derivatization to form a charged species. Thus, the bis-carboxylic acid form of a 40,000 Da PEG has the same charge to mass ratio as the mono-acid form of a 20,000 Da MPEG. Since this relationship remains constant regardless of the derivative utilized, there is minimal expectation that the nature of the derivative (assuming a complete reaction is carried out) will provide a great differential improvement in the separation characteristics of the PEG contaminant in a MPEG product.

It is known that in ion exchange of small molecules that divalent ions are quite strongly retained in comparison to monovalent ions. The assumption is that the ion may be able to interact with two or (more) exchange sites at once and that the ion must be "free" of both sites simultaneously to incrementally move through the matrix. When the two charges are situated at the opposite ends of a polymer chain such as with a PEG di-acid, the two ends seem to function quite independently and the large PEG mass supported by the ionic interaction gives a relatively weak interaction.

The use of PEG to produce MPEG as is described in the '816 application has the advantage that both the MPEG and the PEG materials that are produced have the same molecular weight distribution. The high yield and high volume purification of the PEG contaminant of standard MPEG products produced from ethylene oxide is a more difficult task due to the PEG having, after conversion to a charged derivative, the same charge to mass ratio as the MPEG.

We have prepared derivatives of the polymer to be purified in which the resultant product has at each site of substitution the property of possessing more than a single charge site. When undertaking the derivatization for reasons of purification, it is important that the chemical group added to the polymer be added in such a way as the desired polymer can be recovered after being purified by ion exchange chromatography. Thus the derivatization is essentially one that is chemically reversible.

In certain instances and for purely analytical use, it is not necessary for the derivative to be reversed to be useful or even to be reversed at all. It is found that in the production of modified polymers, a desired form of a polymer may be formed that no longer will react with the derivatization reagent while unreacted or unconverted starting material and/or impurities formed in the chemical reaction(s) used to form the desired product will react to form the derivatives of the invention. In these instances, the desired product will remain un-modified and can be purified from the reactive components in the impure reaction mixture by ion exchange chromatography. Since the derivatized materials are not the desired product, there is no requirement for the chemistry of formation of the derivatives in this instance to be reversible.

What is required is that the chemistry of derivatization can be taken to a high degree of completion so as to allow a high level of purification in the ion exchange chromatography or a high level of accuracy when used as an analytical tool in analytical ion exchange chromatography of polymers. Since the ion exchange chromatography will not separate a PEG molecule which has been only derivatized on one of its terminal groups from a MPEG molecule that has been derivatized on its single reactive site, only a small portion of the reactive sites can be left unmodified for best results. Typically, as long as at least 95% of all reactive groups are derivatized, at least a ten fold reduction in PEG content in a MPEG sample is theoretically possible. This will take an unacceptable MPEG product containing 4% PEG to an acceptable product with less than 0.5% PEG.

When such derivatives are produced as mixtures of PEGs where in the number of reactive terminal groups (or end groups) present varies—the primary example being a mixture of PEG and MPEG—and these derivatives are capable of possessing two or more ionic charges, these derivatives are significantly more readily separated according to the number of end groups derivatized than for analogous species with only a single charge. Purification of MPEG by removal of PEG can be done using 1,2,4-benzene tricarboxylic acid anhydride, shown below as Formula 2 (CAS #552-30-7) to form a reversible ester derivative of all available polymer hydroxyl groups. These derivatives can have two anionic charges for each group substituted. Thus, the resulting MPEG has two negative charges while the PEG impurity has four negative charges (at appropriate pH values in aqueous media). Another multiply charged acid material is shown below as Formula 3, having the chemical name: 1,2,4,5-benzene tetracaboxylic acid dianhydride (CAS #89-32-7). The exemplary compounds shown as Formula 2 or Formula 3 can be used to derivatize a polymer mixture, for example, a mixture containing primarily MPEG with PEG as a contaminant, in order to separate the species within the mixture, according to the methodology described herein.

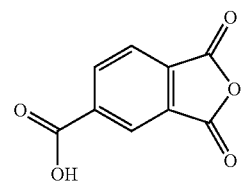

Formula 2

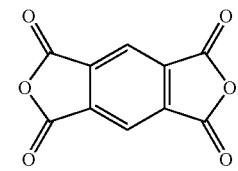

Formula 3

The examples below show results using various molecular weight polymers and derivatives to provide a high resolution analysis of polymers. The use of such derivatives and ion exchange can be applied to the purification of reaction mixtures produced from relatively pure polymers, such as MPEG, wherein the components of the mixture differ in the number of sites that can be derivatized. Such mixtures are highly purified after derivatization as described herein, because once derivatized, multiple ionic charged sights are present at each point of attachment in a polymer molecule, rendering it separable from underivatized polymer.

Unless otherwise noted, all HPLC chromatograms were produced using an evaporative light scattering detector (ELSD). Unless otherwise noted, areas are reported as the area % each peak represents of the total area of all polymer containing peaks. Although the ELSD response is not fully linear, it is monotonic, with lower area % representing less relative amount of a material than other samples with higher area % values for a component. The Refractive Index detector is generally assumed to be linear with respect to polymer concentration and, for example, the SEC result of Example 3 showed only 0.2% PEG remaining in the purified MPEG product and confirms the high level of purification seen when using ELSD as a detector.

Abbreviations used herein are meant to be as understood by a person skilled in the art. Additionally, the following definitions indicate specific intended meaning of select abbreviations used. Buffer A, 0.0004M ammonium acetate 20% MeOH solution. Buffer C, 0.006 M ammonium acetate 20% MeOH solution. Buffer B, 0.4M ammonium acetate 20% MeOH solution. As used herein, Da means Dalton; DIEA, diisopropylethylamine; EDAC, 1-ethyl-3-(3-dimethylaminopropyl)carbodiimide hydrochloride; ELSD, evaporative light scattering detector; Eq, equivalents; kDa, kiloDalton; MeOH, methanol; MES, 2-(N-morpholino)ethane sulfonic acid; MPEG, poly(ethylene glycol) monomethyl ether; mS, milliSeimen; MTBE, tertiary-butyl methyl ether; $NH_4OAc$, ammonium acetate; NHS, N-hydroxylsuccimide; PEG, poly (ethylene glycol); RI, Refractive Index; SEC, Size exclusion chromatography; TEA, triethylamine; THF, tetrahydrofuran; μL, microlitre; DI water, deionized water; $Na_2SO_4$, sodium sulphate; $SOCl_2$, thionyl chloride; KBr, potassium bromide; and KOH potassium hydroxide. The term polyethylene glycol is used here as a synonym for poly(ethylene glycol) and both terms refer to compound 1A as well as does the abbreviation PEG defined above. Synonyms for MPEG, poly(ethylene glycol) monomethyl ether, include: methoxy PEG, MeO-PEG, PEG monomethylether and mPEG.

CAS numbers of select compounds referred to herein are as follows: 1,2,4-benzene tricarboxylic anhydride, 552-30-7; succinic anhydride, 108-30-5; phthalic anhydride, 85-44-9; triethylamine, 121-44-8; ammonium acetate, 631-61-8; and MPEG (regardless of Mw), 9004-74-4; ammonium thiocyanate, 1762-95-4; 1,2,4,5-benzenetetracarboxylic dianhydride, 89-32-7; cobalt (II) nitrate hexahydrate, 10026-22-9; diisopropylethylamine, 7087-68-5; 1,2-dimethylpropyl amine, 598-74-3; 1-ethyl-3-(3-dimethylaminopropyl)carbodiimide hydrochloride, 25952-53-8; mercaptosuccinic acid, 70-49-5; 4-methoxybenzylamine, 2393-23-9; 2-(N-morpholino) ethane sulfonic acid, 4432-31-9; potassium bromide, 7758-02-3; potassium hydroxide, 1310-58-3; pyridine, 110-86-1; sodium triacetoxyborohydride, 56553-60-74; sulfobenzoic acid potassium salt, 5399-63-3; sulfosuccinic acid, 5138-18-1; thionyl chloride, 7719-09-7.

All references noted herein are incorporated herein by reference.

EXAMPLES

Example 1

Derivatization and Analysis of 30,000 Da MPEG Utilizing Phthalic Anhydride

The preparation of 30,000 Da poly(ethylene glycol) monomethyl ether (MPEG) phthalate ester is typical. Unpurified MPEG 30,000 Da (6.0 g, 0.2 mmol) and phthalic anhydride (0.592 g, 4 mmol) were dissolved in anhydrous tetrahydrofuran (20 mL). Triethylamine (1.37 ml, 10 mmol) was added. The reaction solution was heated to 55° C. and the reaction was stirred for 24 hours. The reaction solution was then cooled and volume of solvent was reduced in vacuo. The polymeric material was precipitated in t-butyl-methyl-ether (MTBE). The white solid was collected by filtration and dried. Yield for the synthesis was 90%.

In a similar manner, phthalic acid esters of MPEG 10,000 Da, MPEG 20,000 Da, PEG 8,000 Da, PEG 20,000 Da and PEG 35,000 Da were prepared.

Ion exchange analysis. A 2 mg/mL sample of the derivatized 10,000 Da MPEG phthalic acid ester material prepared as described above was dissolved in 0.006M ammonium acetate ($NH_4OAc$)/20% methanol buffer (Buffer C) The solution was filtered through a 0.2 μm to produce a sample for injection. Ten (10) μL of the sample was injected into a mobile phase of 0.006M ammonium acetate buffer (Buffer C) and of 0.4M ammonium acetate buffer (Buffer B) at a flow rate of 0.2 mL per minute and flowed through a Sepax Proteomix™ SAX-NP3 ion exchange column (4.6×150 mm) and into an evaporative light scattering detector (ELSD). The ELSD was routinely set at 2.9 bars nitrogen and 90 to 110 degrees C. The ELSD produced a chromatogram as shown in FIG. 1. The monoacid derivatized 10,000 Da MPEG, MPEG phthalate, eluted with a retention time of 4.88 minutes.

The monoacid derivatized 20,000 Da MPEG and 30,000 Da MPEG eluted with retention times of 4.33 and 4.19 minutes respectively. The corresponding 8,000, 20,000 and 35,000 Da PEG derivatives eluted with retention times of 8.14, 4.85 and 4.40 minutes. These PEG derivatives possessed an ester bonded phthalate group capable of possessing a single negative charge at each end of the polymer chain.

Figure 2A:
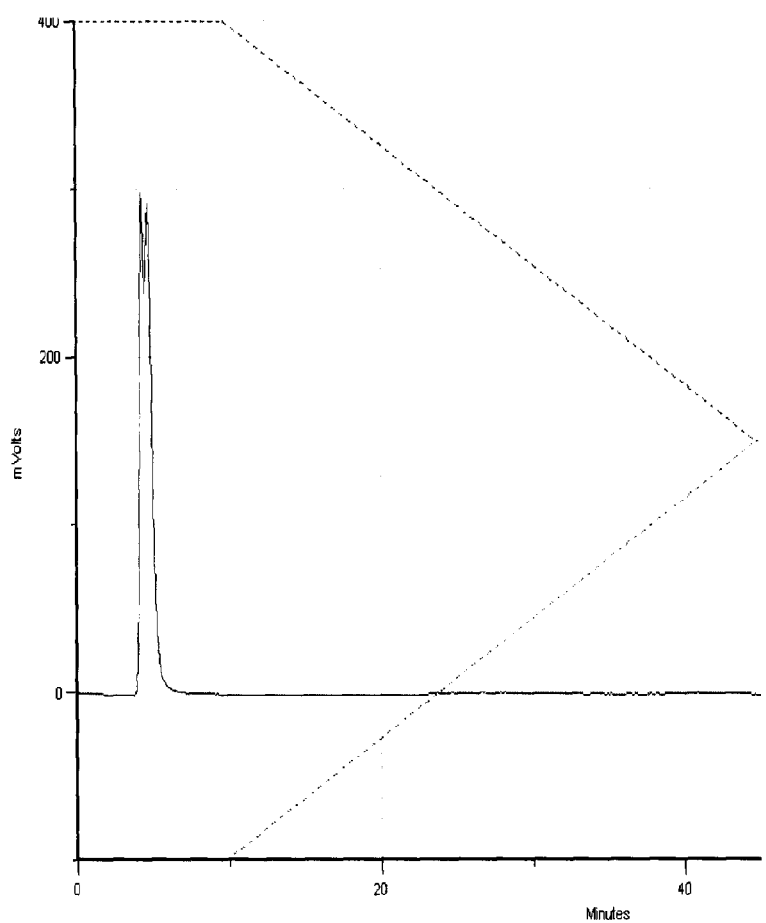
FIG. 2A is a chromatogram of phthalic acid derivatized 10,000 Da and 20,000 Da MPEG and 20,000 Da and 35,000 Da PEG according to Example 1.
Figure 2B:
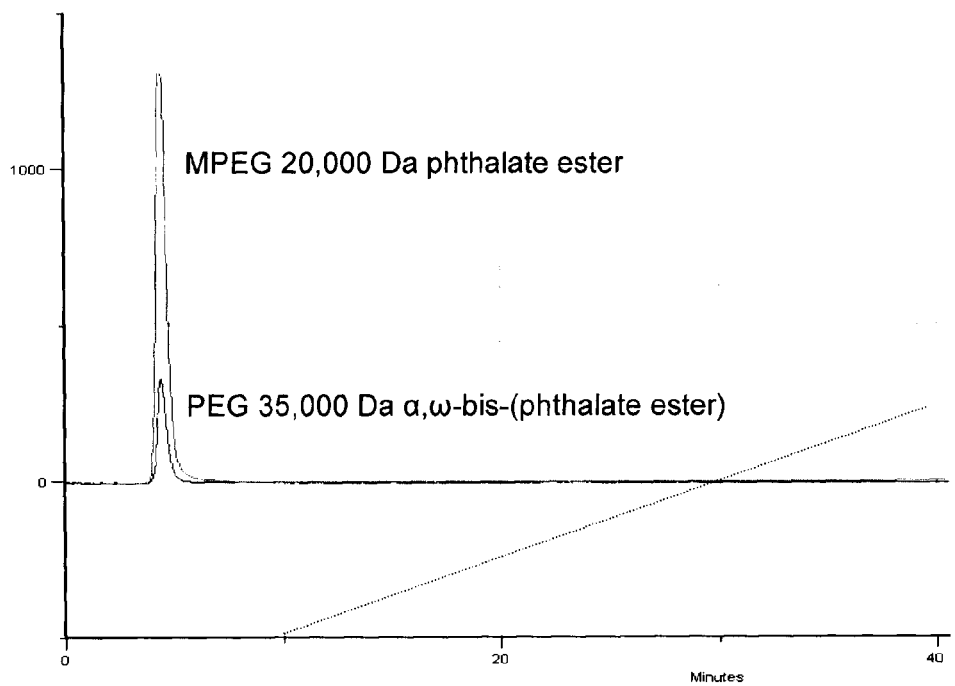
FIG. 2B shows an overlay of 20,000 Da MPEG phthalate ester and 35,000 Da PEG α,ω-bis-(phthalate ester) according to Example 1.

A chromatogram of phthalic acid derivatized 10,000 Da and 20,000 Da MPEG and 20,000 Da and 35,000 Da PEG is shown in FIG. 2A. This chromatogram displays two partially resolved peaks. Injections of the individual components confirm that the first peak is composed of the 20,000 Da MPEG mono-derivative and 35,000 Da di-derivatized species PEG; the second is mono-derivatized 10,000 Da MPEG and 20,000 Da di-derivatized species PEG. FIG. 2B shows an overlay of 20,000 Da MPEG mono-derivative and 35,000 Da di-derivatized PEG. The monocarboxylic acid derivatives are not suitable for purification purposes.

Example 2

Purification of 20,000 MPEG Utilizing 1,2,4-Benzenetricarboxylic Anhydride.

Preparation of MPEG benzene tricarboxylic acid ester 20,000 Da. An 20,000 Da MPEG product was purchased that contained approximately 5% of the high molecular weight PEG typically found in materials produced from ethylene oxide polymerizations. To a clean dry 100 gallon reactor flushed with nitrogen was added anhydrous tetrahydrofuran (THF, 100 L), unpurified MPEG 20,000 Da (10.3 kg, 0.52 moles) and 1,2,4-benzene tricarboxylic anhydride (961 g, 5.0 moles). After complete addition, the mixture was stirred and the temperature was maintained between 5° C. and 15° C. Triethylamine (145 mL, 1.0 moles) was then added. The mixture was heated to reflux (75-85° C.) and stirred under a nitrogen atmosphere for 20 hours. After removal of the THF by distillation, the reactor was cooled to 45° C., MTBE (200 L) was added over a 30 min period to precipitate the MPEG and PEG derivatives. The mixture was further cooled to 0-5° C. The resultant precipitate was collected and dried under vacuum at 30° C. for 24 hours. The dried crude product was dissolved in an aqueous sodium chloride solution (15%, pH adjusted to 2.0) and stirred for 1 hour. Dichloromethane was used to extract the desired PEG derivatives (3×35 L). The organic layer was collected and washed with aqueous sodium chloride solution (15%) and dried over anhydrous sodium sulfate. The slurry was filtered and the filtrate collected. Dichloromethane was removed until the volume of the solution was reduced to ~35 L. The remaining mixture was cooled to 30° C. and MTBE (120 L) was added to precipitate the PEG derivatives. The reactor was further cooled to 0-5° C. and the precipitate was collected. After drying under reduced pressure for 24 hours, the derivatized MPEG/PEG material was collected (9.16 kg, 91.6% yield).

Figure 3:
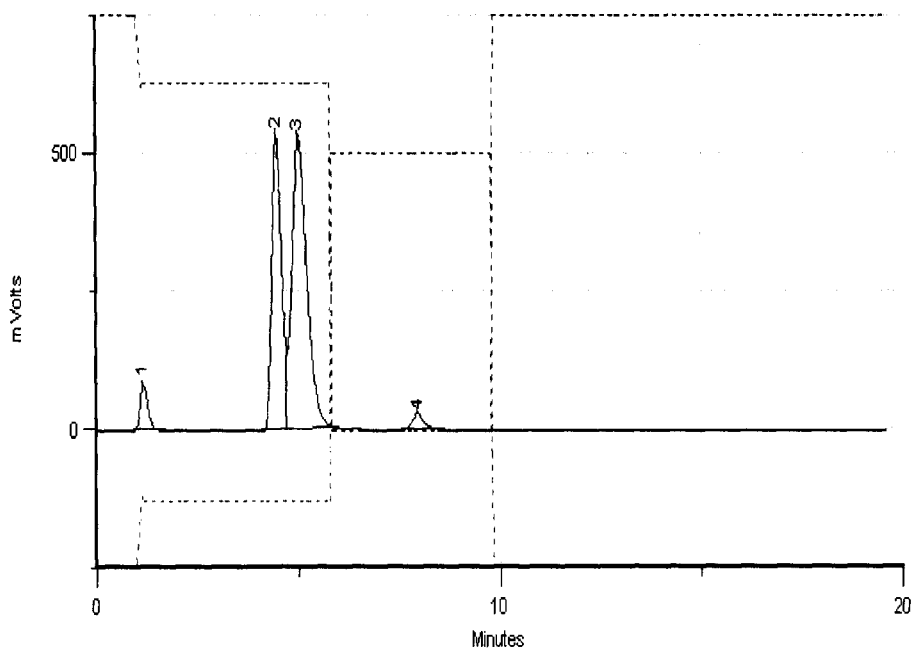
FIG. 3 provides a chromatogram based on a two step buffer gradient. Neutral material represents 4.70% of the area of all peaks, MPEG benzene tricarboxylic acid ester 20,000 Da represents 92.72% of the unpurified mixture.

Ion exchange analysis: A 6.7 mg sample of the derivatized MPEG/PEG material was dissolved in 1.68 mL 0.0004M ammonium acetate ($NH_4OAc$) buffer. The solution was filtered through a 0.45 μM filter to produce a sample for injection. Ten microliters of the sample was injected into a mobile phase of 0.0004M ammonium acetate buffer (Buffer A) and of 0.4M ammonium acetate buffer (Buffer B) at a flow rate of 0.9 mL per minute and flowed through a Mono Q™ 4.6/100 PE anion column (4.6×100 mm) and detected using an ELSD. With a two step buffer gradient, a chromatogram as shown in FIG. 3 was produced. Neutral material represents 4.70% of the area of all peaks, MPEG benzene tricarboxylic acid ester 20,000 Da represents 92.72% (sum of the two isomers with retention times of 4.45 and 5.01 min. in FIG. 3). The remaining material was PEG derivatives of long retention time showed 2.59% of the area at 7.95 min.

Chromatographic separation of the unpurified MPEG benzene tricarboxylic acid ester 20,000 Da. A column 60 cm in diameter was packed with 60 L of Q-Sepharose Fast Flow ion exchange resin (GE Biosciences) and used for purification of the MPEG benzene tricarboxylic acid ester. Prior to loading the unpurified MPEG benzene tricarboxylic acid ester, the resin was regenerated with 375 mM ammonium acetate solution (5.2 kg ammonium acetate/180 L deionized water, at least 3 bed volumes utilized) and washed with deionized water until the conductivity measurements are less than 0.020 milli-Seimen (mS). A solution of unpurified MPEG benzene tricarboxylic acid ester 20,000 Da in deionized water (1.8 kg/45 L DI water=40 g/l) was prepared and loaded onto the prepared column at a flow rate between 0.8 to 1.2 L/min. The conductance of a typical sample prepared at this concentration was 0.32 mS. The neutral PEG was eluted with 50 L of deionized water.

A cobalt test was conducted to estimate poly(ethylene glycol). Briefly, cobalt test solution is used for the colorimetric assay for estimation of poly(ethylene glycol). Cobalt (II) nitrate hexahydrate (1.5 g, 0.0052 mol) and ammonium thiocyanate (10 g, 0.104 mol) were dissolved in deionized water (50 mL). Use an equivolume amount of cobalt test solution and eluate. A pink colour result (negative) indicates absence of PEG material; a blue coloration (positive test) indicates presence of PEG material. Strong positives yield a precipitate.

After a negative cobalt test result confirmed that all neutral material had been washed off, the product was eluted with a 4 mM ammonium acetate solution (46.2 g/150 L deionized water) at a flow rate between 1.0 to 1.4 L/min. The conductivity of this solution was 498 mS. The eluate was collected from the column in 10 L fractions. Each fraction was tested using the cobalt test and positive fractions pooled. Product was present in 130 L of eluent.

Figure 4:
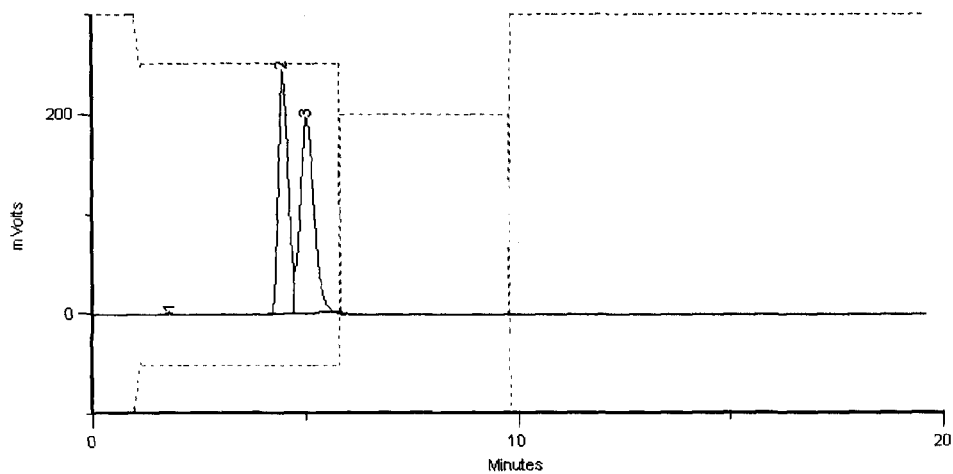
FIG. 4 is a representative chromatogram of a collected fraction, containing MPEG 20,000 Da benzene tricarboxylic acid ester, using a typical two step gradient as in Example 2.
Figure 5:
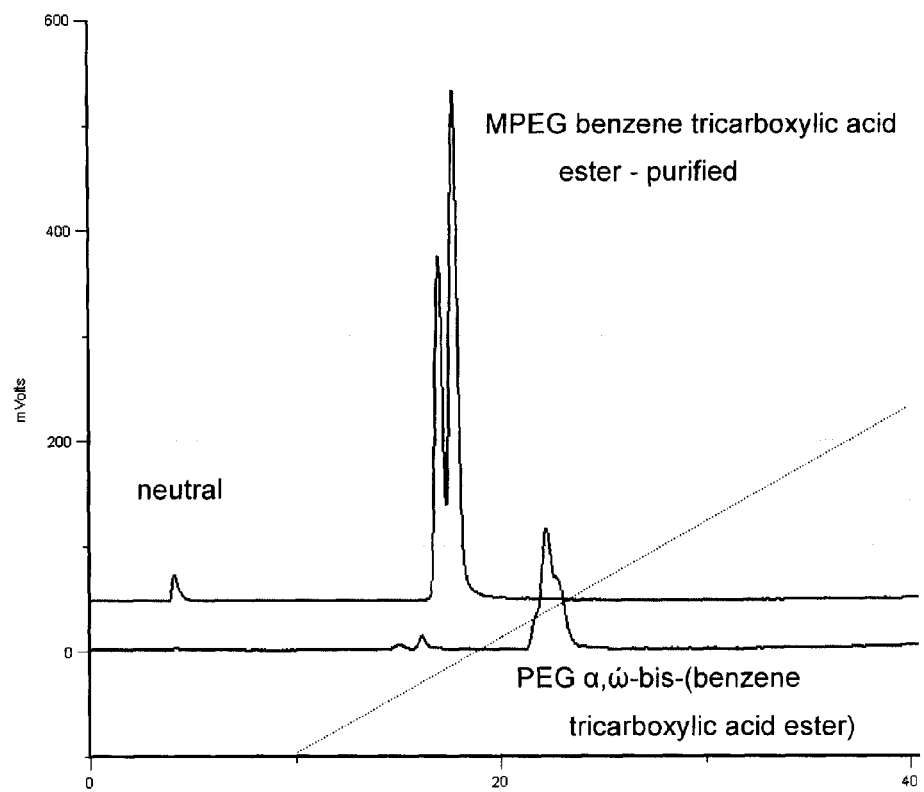
FIG. 5 is an overlay of individual chromatograms for purified MPEG 20,000 Da benzene tricarboxylic acid ester and PEG 35,000 Da α,ω-bis-(benzene tricarboxylic acid ester) according to Example 2.

Ion exchange analysis. FIG. 4 is a representative chromatogram of a collected fraction using a typical two step gradient chromatography conditions. For more direct comparison of the binding strength, the materials were also chromatographed using a linear gradient elution profile. This allows an estimation of the strength of binding based on the salt concentration required to elute the various PEG and MPEG derivatives. With a linear gradient of buffer, MPEG 20,000 Da diacid isomers have retention times of 17.01 and 17.73 minutes. With the same gradient, PEG 35,000 Da α,ω-bis-(benzene tricarboxylic acid ester) has a retention time of 20.47 minutes. FIG. 5 is an overlay of these two linear gradient chromatograms.

Preparation of purified MPEG 20,000 Da. Fractions containing desired purified MPEG benzene tricarboxylic acid ester 20,000 Da were combined from 5 separate chromatographic separation steps to yield 594 L of solution. These product containing fractions were treated with sodium hydroxide (640 g) and the volume reduced to 80 L via a slow distillation of the water under reduced pressure. The reaction vessel was cooled to between 5 and 15° C. and hydrochloric acid (ca. 1.27 L) was added to the solution until a pH of 5.3 was achieved. The solution was warmed to 20° C. and sodium chloride (12 kg) was added. Product was extracted into dichloromethane (2×50 L); the organic layer was collected and dried over anhydrous sodium sulfate (5 kg). The resultant slurry was filtered and the cake washed with methylene chloride (10 L). The filtrate was collected and the volume of dichloromethane was reduced to 30 L by vacuum distillation. Upon cooling to 30° C., MBTE (120 L) was added and a precipitate formed. After complete addition of the MTBE, the temperature was lowered to between 5 and 0° C. for one hour. The resultant precipitate was collected by filtration and dried under vacuum at 30° C. for 24 hours. Yield was 93.4% for this process step. Overall yield of the purified MPEG 20,000 Da (5.66 kg) was 55%.

Ion exchange analysis. The purified non-derivatized MPEG 20,000 Da had a chromatogram with a 100 area % peak eluting with a retention time of 1.15 minutes with 100% of buffer A.

SEC analysis. By SEC analysis using RI detection, raw starting material had 95.2% MPEG (area percent as measured by refractive index) with a molecular weight (Mn) of 20,228 Da and 4.8% of PEG material with high molecular weight of greater than 42,000 Da. Area percent is determined by dividing the peak area of the peak under study by the combined peak areas of all medium to high molecular weight peaks (i.e. all peaks eluting with an elution volume less than a 2,000 Da PEG standard). After derivatization, purification and removal of the carboxylic acid group, the amount of high molecular weight PEG material was reduced to 0.2% (Chromatograms not shown).

Example 3

Purification of 10,000 Da MPEG Utilizing 1,2,4-Benzenetricarboxylic Anhydride.

Preparation of MPEG benzene tricarboxylic acid ester 10,000 Da. An 10,000 Da MPEG product was purchased that contained over 5% of the high molecular weight PEG typically found in materials produced from ethylene oxide polymerizations. Unpurified MPEG 10,000 Da (15 kg, 1.5 moles) contaminated with high and low molecular weight PEG material was added to a previously cleaned dried 100 gallon reactor with anhydrous tetrahydrofuran (THF, 100 L) and 1,2,4-benzene tricarboxylic anhydride (2880 g, 15 moles). After complete addition, the mixture was stirred and the temperature was maintained between 5° C. and 15° C. under a nitrogen atmosphere. Triethylamine (435 mL, 3 moles) was to the reaction mixture. The reaction mixture was heated to reflux (75-85° C.) and stirred under a nitrogen atmosphere for 24 hours. After this period, THF (33 kg) was removed with distillation and the reactor was cooled to 45° C. MTBE (300 L) was added over a 30 min period to precipitate the MPEG (and PEG) derivatives. The mixture was further cooled to 0-5° C. The resultant precipitate was collected and dried under vacuum at 30° C. for 24 hours. The dried crude product was dissolved in an aqueous sodium chloride solution (15%, pH adjusted to 2.0) and stirred for 1 hour. The PEG derivatives were extracted into dichloromethane (3×50 L). The organic layer was collected and washed with aqueous sodium chloride solution (15%) and dried over anhydrous sodium sulfate. The slurry was filtered and the filtrate collected. Dichloromethane was removed until the volume of the solution was reduced to ~35 L. The remaining mixture was cooled to 30° C. and MTBE (140 L) was added to again precipitate the prepared polymeric derivatives. The reactor was further cooled to 0-5° C. and the precipitate was collected by filtration. After drying for 24 hours, the derivatized MPEG/PEG material was collected (13.92 kg, 92.8% yield).

Figure 6:
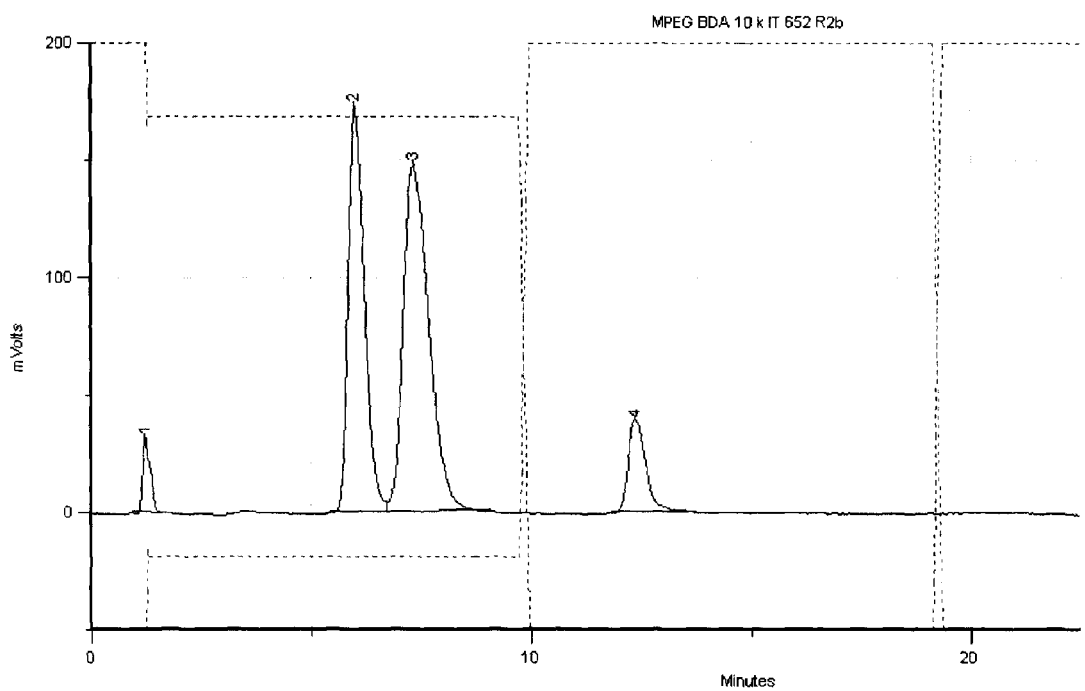
FIG. 6 shows a chromatogram of unpurified MPEG 10,000 Da benzene tricarboxylic acid esters according to Example 3. The presence of PEG as PEG α,ω-bis-(benzene tricarboxylic acid ester) is shown by the peak at 12.40 min.

Ion exchange analysis: A 9 mg sample of the derivatized MPEG/PEG material was dissolved in 2.25 mL 0.0004M ammonium acetate ($NH_4OAc$) buffer. The solution was filtered through a 0.2 µm to produce a sample for injection. Ten microliters of the sample was injected into a mobile phase of 0.0004M ammonium acetate buffer (Buffer A) and of 0.4M ammonium acetate buffer (Buffer B) at a flow rate of 0.9 mL per minute and flowed through a Mono Q™ 4.6/100 PE anion column (GE Biosciences, 4.6×100 mm). The ELSD produced the chromatogram shown in FIG. 6. The neutral underivatized species represents 3.14% of the total area, MPEG (10,000 Da) benzene tricarboxylic acid ester (two isomers) represents 87.47% of the area percent. The α,ω-bis-(benzene tricarboxylic acid ester) derivatized PEG impurities are more retained and represent 9.40%.

Chromatographic separation of the unpurified MPEG benzene tricarboxylic acid ester. Q-Sepharose Fast Flow ion exchange resin (54 L) was used for purification of the MPEG benzene tricarboxylic acid ester. Prior to loading the unpurified MPEG benzene tricarboxylic acid ester, the resin was regenerated with 375 mM ammonium acetate solution (5.2 kg ammonium acetate/150 L deionized water) and washed with deionized water until the conductivity measurements are less than 0.020 mS. A solution of unpurified MPEG benzene tricarboxylic acid ester 20,000 Da in deionized water (2.16 kg/55 L DI water=40 g/l) was prepared and loaded onto the prepared column at a flow rate between 1.0 to 1.4 L/min. The column was eluted with 50 L of deionized water and samples of the wash were tested using the cobalt test to test for any PEG derivative. After a negative cobalt test result, the column was eluted with 8 mM ammonium acetate solution at a flow rate between 1.0 to 1.4 L/min. The eluate was collected from the column in 10 L fractions. Each fraction was tested using the cobalt test. The collected fractions are analyzed using ion exchange chromatography with an ELSD. Product was determined in 89.8 L of eluent.

Figure 7:
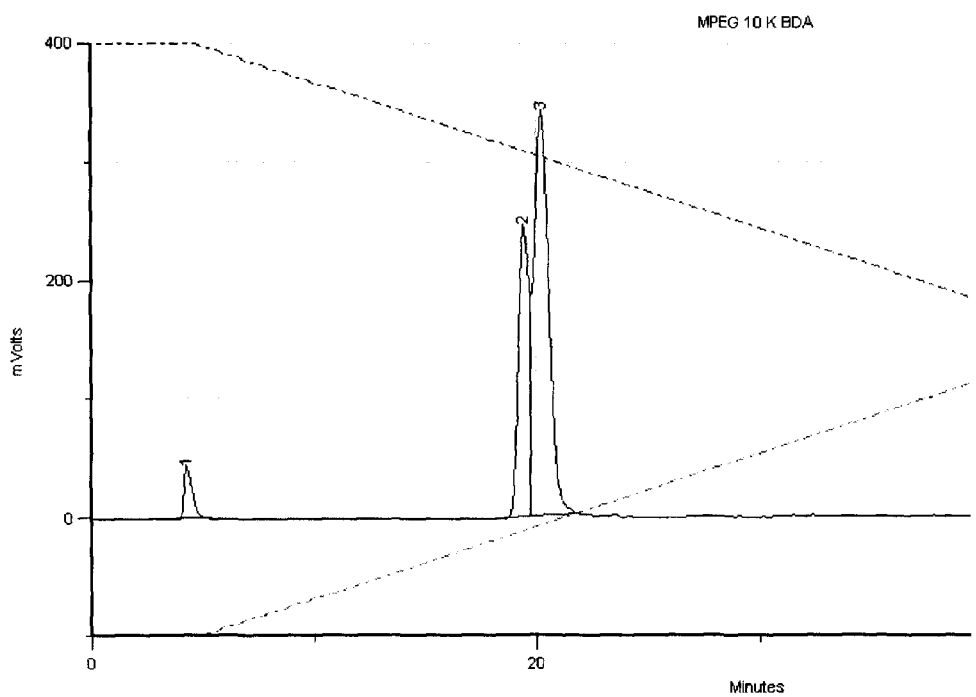
FIG. 7 shows a chromatogram of the purified 10,000 Da MPEG benzene tricarboxylic acid ester according to Example 3.
Figure 8:
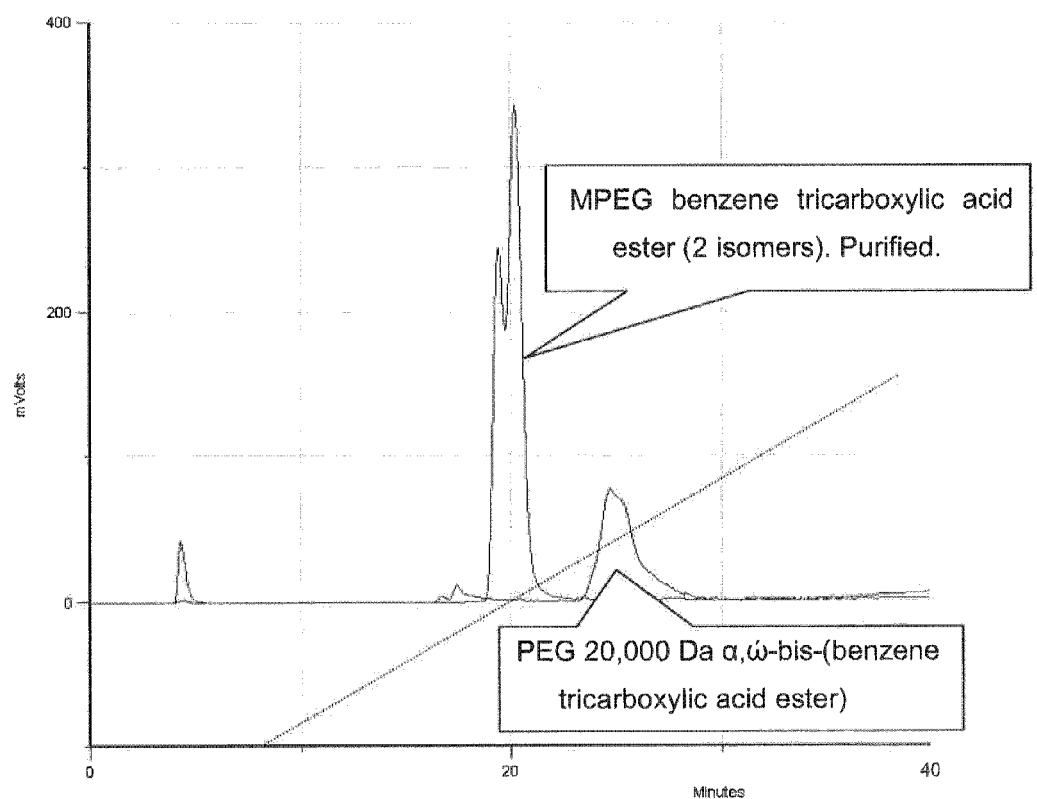
FIG. 8 is an overlay of individual chromatograms of purified MPEG 10,000 Da benzene tricarboxylic acid ester and PEG 20,000 Da α,ω-bis-(benzene tricarboxylic acid ester) according to Example 3.

Ion Exchange Analysis. A chromatogram of the purified 10,000 Da MPEG run as a linear gradient is represented in FIG. 7. With this linear gradient, MPEG 10,000 Da diacid isomers have retention times of 19.41 and 20.19 minutes. With the same gradient, PEG 20,000 Da α,ω-bis-(benzene tricarboxylic acid ester) has a retention time of 24.50 minutes. FIG. 8 is an overlay of these chromatograms.

Preparation of purified MPEG 10,000 Da. Fractions containing desired purified MPEG benzene tricarboxylic acid ester 10,000 Da were combined (500 L), treated with sodium hydroxide (960 g) and the volume reduced to 80 L with a slow distillation of the solvent under reduced pressure. The reaction vessel was cooled to 10±5° C. and hydrochloric acid (1.9 L) was added slowly to the solution until a pH of 2.82 was achieved. The solution was warmed to 20° C. and sodium chloride (18 kg) was added. Dichloromethane (2×70 L) was added and the solution was agitated. The organic layer was collected and dried over anhydrous sodium sulfate (7.5 kg). The resultant slurry was filtered and washed with methylene chloride (15 L). The filtrate was collected and the volume of dichloromethane was reduced to 30 L by distillation. Upon cooling to 30° C., MTBE (140 L) was added slowly and a precipitate formed. After complete addition of the MTBE, the temperature was lowered to ~0° C. for an hour. The resultant precipitate was collected by filtration and dried under vacuum at 30° C. for 24 hours. Yield was 79.5% for this process step. Overall yield of the purified MPEG 10,000 Da (6.68 kg) was 44.5%.

SEC Analysis. By SEC analysis using RI detection, raw starting material had 94.9% MPEG (area percent as measured by refractive index) with a molecular weight (Mn) and 5.1% of PEG material with high molecular weight. SEC analysis of the purified non-derivatized MPEG 10,000 Da demonstrated the MPEG as 99.8% pure.

Example 4

Purification of 30K MPEG Utilizing 1,2,4-Benzenetricarboxylic Anhydride with 1,2,4-Benzenetricarboxylic Acid.

Preparation of MPEG benzene tricarboxylic acid ester derivative. 30,000 Da MPEG product was purchased that contained over 7% of the high molecular weight PEG typically found in materials produced from ethylene oxide polymerizations. The purchased material (304 g) was converted to a mixture of MPEG diacids and PEG tetra acids by reaction with 19.5 g of 1,2,4-benzene tricarboxylic anhydride in 3 L of tetrahydrofuran. Triethylamine (8.5 ml) was added to neutralize the excess acid. The mixture was stirred for 78 hours at reflux (ca. 69° C.). The mixture of polymeric products was concentrated to a volume of 1.5 L total and precipitated by the addition of 6 L of MTBE and filtered. The product was washed with 2×500 ml MTBE and dried under vacuum at 30° C. for 18 hours. The crude product was dissolved in 3 L of aqueous sodium chloride (15% NaCl, pH adjusted to 2.0 with HCl). The acidified product was extracted into dichloromethane (3×1 L). The dichloromethane was washed once with 1.4 L of the fresh acidic brine. The dichloromethane was dried with sodium sulfate (250 g), filtered and combined with two 250 ml washes of the drying agent. The solution was concentrated to a final volume of 750 ml. The product was precipitated with 3 L of MTBE. The solid was filtered and washed with 500 ml MTBE. After drying, 293.5 g or >96% of the original MPEG weight was recovered. The PEG present in the starting material is converted to a mixture of the α,ω-bis-(benzene tricarboxylic acid ester) derivatives, each derivative (multiple isomers are possible to form but poorly resolved chromatographically) capable of having four anionic charges.

Figure 9:
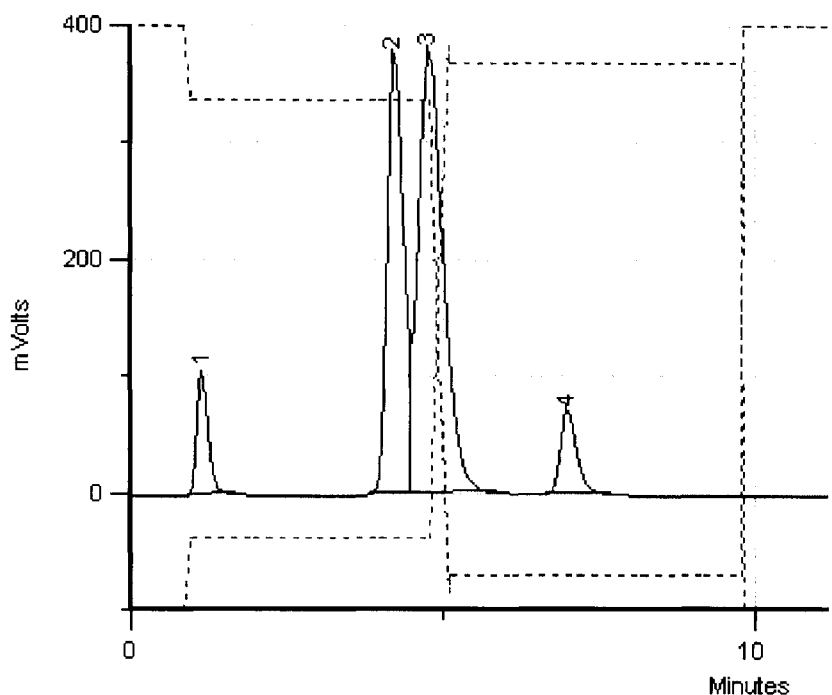
FIG. 9 shows a chromatogram of unpurified MPEG 30,000 Da benzene tricarboxylic acid ester according to Example 4. Peak 4 is PEG derivative and is 6.46% of the area.

Ion exchange analysis. A 8 mg sample of the derivatized MPEG/PEG material was dissolved in 2.00 mL 0.0004M ammonium acetate ($NH_4OAc$) buffer. The solution was filtered through a 0.2 µm to produce a sample for injection. Ten (10) ul of the sample was injected into a mobile phase of 0.0004M ammonium acetate buffer (Buffer A) and of 0.4M ammonium acetate buffer (Buffer B) at a flow rate of 0.9 mL per minute and flowed through a Mono Q™ 4.6/100 PE anion column (4.6×100 mm). An evaporative light scattering detector (ELSD) produced a chromatogram as shown in FIG. 9. The neutral underivatized species represents 6.65% of the total area, MPEG (30,000 Da) benzene tricarboxylic acid ester represent 86.89% of the area. The α,ω-bis-(benzene tricarboxylic acid ester) PEG impurities are more retained and represent 6.46%.

Chromatographic separation of the unpurified MPEG benzene tricarboxylic acid ester. The mixture of MPEG and PEG acid derivatives obtained above, 100 g, was dissolved in 2.5 L of deionized water. The solution was applied to a column containing 5 L of the anion exchange medium Q-Sepharose Fast Flow. Before use, the column had been washed with 0.375 M ammonium acetate solution (7.5 L) and with 10 L of deionized water. The sample was applied at a flow rate of approximately 125 ml/min. Following application of the sample, the column was eluted with approximately 5 L of deionized water. The wash was continued until no polymer is detected using the cobalt color test. This water eluted fraction contains neutral polymer material and any un-derivatized MPEG or PEG. The column is then eluted and collected in nine fractions of 1.5 to 3.5 L using 0.004 M ammonium acetate. The derivative also has UV absorption and relative concentration can be estimated by measuring the absorbance at 240 nm. Fractions having an optical density at 240 nm greater than 0.325 were pooled (fractions 5, 6 and 7). These fractions totaled 7.75 L. The column was then washed with 0.375 M ammonium acetate until the eluate was negative for the presence of polymer using the cobalt color test. Two such experiments were run and the material eluting with 0.375 M ammonium acetate was pooled, concentrated and recovered by extraction with dichloromethane as previously described. This material was the PEG material present. SEC analysis confirmed the presence of a high concentration of 60,000 Da material as well as lower molecular weight PEG derivatives.

Preparation of purified MPEG 30,000 Da. The fractions 5, 6 and 7 eluted with 0.004 M ammonium acetate were concentrated to about 1 L and treated with 8.0 grams of sodium hydroxide. The solution was stirred overnight at ambient temperature to hydrolyze the ester bond holding the MPEG to the tri-acid reagent. The pH was adjusted to 5.1 with concentrated HCl and sodium chloride was added (150 g). This mixture was extracted with 2×1 L dichloromethane. The dichloromethane was dried using sodium sulfate (103 g) and the sodium sulfate filtered and washed with 2×100 ml dichloromethane. The dried dichloromethane solution was concentrated under vacuum to a volume of 600 ml and 2.2 L of MTBE was added. The solution was cooled to 0° C. for 1 hour, filtered and the product washed with 200 ml of MTBE. Drying yielded 70.0 g of purified 30,000 Da MPEG (70% yield).

SEC Analysis. SEC analysis using RI detection showed that the high molecular weight PEG found at ca 62,000 Da had been lowered from 7.2% (area %) as purchased to 0.87% in the purified product described herein.

Example 5

Preparation and Purification of 30,000 Da MPEG Utilizing Benzene-1,2,4,5-Tetracarboxylic Dianhydride Preparation of 30,000 Da MPEG benzene tetracarboxylic acid ester. A series of MPEG and PEG benzene tricarboxylic acid esters was synthesized. A representative example is the reaction of 30,000 Da MPEG with benzene-1,2,4,5-tetracarboxylic dianhydride. Anhydrous tetrahydrofuran (THF, 50 mL) was added to purchased 30,000 Da MPEG (12.06 g, 0.40 mmol) and benzene-1,2,4,5-tetracarboxylic dianhydride (1.74 g, 8.0 mmol) under a dry atmosphere. The reaction vessel was heated to 50° C. and the solid materials dissolved. Triethylamine (12.74 mL, 20 mmol) was added to the solution and stirring was continued for 30 hours. After this time, the solvent volume was reduced by half and MTBE was used to precipitate the polymeric compounds. The precipitate was filtered, washed and dried under vacuum at 30° C. Yield of the reaction was 97.6%.

Purification of 30,000 Da MPEG benzene tetracarboxylic acid ester. Q-Sepharose Fast Flow ion exchange resin (50 mL) was used for purification of the PEG benzene tetracarboxylic acid ester. Prior to loading the unpurified MPEG benzene tetracarboxylic acid ester, the resin was regenerated with 0.375 M ammonium acetate solution (28.9 g ammonium acetate/1 L deionized water) and washed with deionized water until the conductivity measurements are less than 0.020 mS. A solution of unpurified 30,000 Da MPEGbenzene tetracarboxylic acid ester in deionized water (1.06 g/26.5 mL DI water=40 mg/mL) was prepared and loaded onto the prepared column at a flow rate 4 mL/min. Neutral polymer was eluted with 80 mL of deionized water. This water eluted fraction contains neutral polymer material and any un-derivatized MPEG or PEG. After a negative cobalt test result indicating that all neutral material had been washed off, the MPEG benzene tetracarboxylic acid ester product was eluted with a 0.10 M ammonium acetate solution at the same flow rate. The eluate was collected from the column in 10 mL fractions. Each fraction was tested using the cobalt test. Product was present in approximately 30 mL of eluate. The fractions containing product were pooled, concentrated and extracted with dichloromethane. The dichloromethane was removed by evaporation at reduced pressure. The residue was redissolved in 5 ml of dichloromethane and precipitated by addition of MTBE, filtered and dried. The 30,000 Da MPEG benzene tetracarboxylic acid ester was recover in 58% yield (580 mg).

Figure 10:
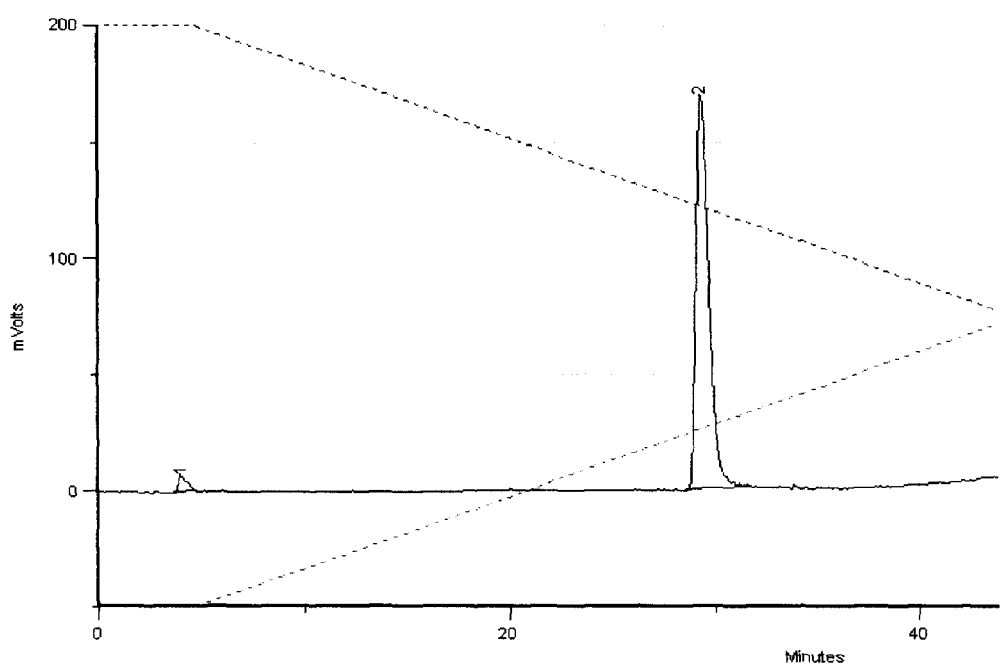
FIG. 10 shows a chromatogram of MPEG 30,000 Da benzene tetracarboxylic acid ester according to Example 5.

Ion exchange analysis: A 6.3 mg sample of the derivatized material was dissolved in 1.26 mL 0.0004M ammonium acetate ($NH_4OAc$) buffer. The solution was filtered through a 0.2 μm to produce a sample for injection. A sample of 5 μL of the sample was injected into a mobile phase of 0.006M ammonium acetate buffer (Buffer C) and of 0.4M ammonium acetate buffer (Buffer B) at a flow rate of 0.5 mL per minute and flowed through a Sepax Proteomix SAX-NP3 ion exchange column using ELSD detection to produce the chromatogram shown in FIG. 10. The retention time of the MPEG (30,000 Da) benzene tetracarboxylic acid ester (a trianion) is 29.33 minutes.

Example 6

Derivatization and Analysis of 30,000 Da MPEG-OH Utilizing Succinic Anhydride.

Preparation of 30,000 Da poly(ethylene glycol) monomethyl ether (MPEG) succinic acid ester is typical. Anhydrous tetrahydrofuran (THF, 15 mL) was added to a dry reaction vessel containing unpurified MPEG (30,000 Da, 3 g, 0.1 mmol). Succinic anhydride (0.20 g, 2 mmol.) was added to the reaction vessel and the reaction was heated to 55° C. All solid material dissolved with stirring. Triethylamine (0.70 mL, 5.0 mmol) was added to the solution and the reaction was stirred for 24 hours. The reaction was cooled to room temperature and the polymeric products came out of solution. Dichloromethane (5 mL) was added to solubilize the material. The polymeric products were precipitated with MTBE to give a white solid (2.89 g).

A 20,000 Da MPEG succinate ester sample was analyzed via anion exchange liquid chromatography using ELSD detection and indicated 87.57% mono-anion material, 0.91% neutral material and 11.52% α,ω-bis-succinyl ester material arising from PEG present in the MPEG. A prepared analytical sample was flowed through a Sepax Proteomix SAX-NP3 ion exchange column. After a five minute period flowing Buffer C, a linear gradient of increasing concentrations of Buffer B was pumped through the column.

Figure 11A:
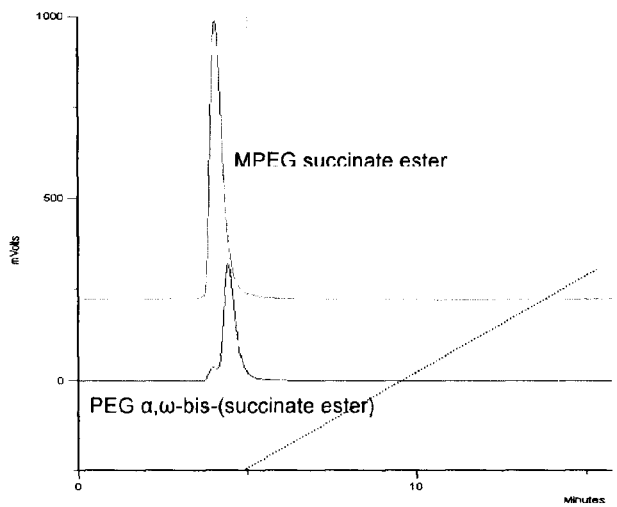
FIG. 11A shows overlays of individual chromatograms of succinic acid derivatives of 20,000 Da MPEG and 35,000 Da PEG.
Figure 11B:
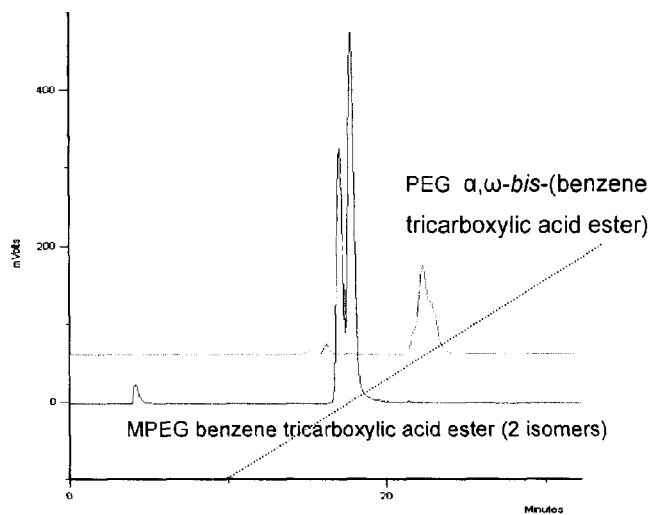
FIG. 11B shows overlays of individual chromatograms of benzene tricarboxylic acid ester derivatized 20,000 Da MPEG and 35,000 Da PEG, according to Example 6. The same linear salt gradient elution was utilized in 11A and 11B.

Similarly, 20,000 Da MPEG, 8,000 Da PEG and 35,000 Da PEG materials were derivatized and analysed. There is no significant difference in retention times of the 20,000 Da MPEG mono-derivatized material and the 35,000 Da PEG bis derivatized material. The low molecular weight 8,000 Da bis derivatized PEG was the most retained material. FIG. 11A shows an overlay of chromatograms of two succinic acid derivatives, the 20,000 Da mono-succinate MPEG and the 35,000 Da α,ω-bis-succinyl ester PEG. The two species have indistinguishable retention times. All monoanionic derivatives eluted before the gradient of Buffer B had reached the detector. FIG. 11B is the corresponding overlay of the 20,000

Da MPEG benzene tricarboxylic acid ester and 35,000 Da PEG α,ω-bis-(benzene tricarboxylic acid ester)

Chromatograms of succinate, phthalate, benzene tricarboxylic acid ester and benzene tetracarboxylic acid ester derivatives were obtained and compared. The retention times of MPEG acid ester derivatives containing one ionizable group are indistinguishable from PEG acid ester derivatives of approximately twice the molecular weight containing two mono-ionizable groups. For derivatives with two or more ionizable groups, e.g. the diacid and triacid ester derivatives of 20,000 Da MPEG, there is sufficient differences in retention time to successfully distinguish the MPEG derivatives from the corresponding derivatized PEG impurities. Retention times for the derivatized 20,000 Da MPEG and 35,000 Da PEG materials are noted in TABLE 1. Since a linear gradient of ionic strength was applied to the column after a 5 minute isocratic period, a retention time over 5 minutes correlates with the salt concentration or ionic strength required to overcome the binding of the polymer to the ion exchange material and thus, to elute the polymer. The longer the retention time, the greater the ionic strength needed for elution and the stronger the binding of the polymer to the ion exchange medium.

TABLE 1

Comparison of Chromatographic Retention Times for 20,000 Da derivatized MPEG and 35,000 Da derivatized PEG

| | | |
|---|---|---|
| MPEG/PEG succinic acid derivatives | 20 kDa MPEG | 35 kDa PEG |
| Retention Time (min) | 4.06 | 4.20 |
| MPEG/PEG pthalic acid ester derivatives | 20 kDa MPEG | 35 kDa PEG |
| Retention Time (min) | 4.23 | 4.43 |
| MPEG/PEG benzene tricarboxylic acid ester derivatives | 20 kDa MPEG (isomers ½) | 35 kDa PEG |
| Retention Time (min) | 17.01/17.73 | 22.05 |
| MPEG/PEG benzene tetracarboxylic acid ester derivatives | 20 kDa MPEG | 35 kDa PEG |
| Retention Time (min) | 29.82 | 44.36 |

Example 7

Influence of Number of Ionizable Groups on the Ion Exchange Binding for MPEG and PEG Derivatives Prepared According to the Invention.

Derivatives were prepared and eluted from SEPAX™ ion exchange resin. Table 2 describes the concentration of salt necessary to elute exemplary acid ester derivatives of MPEG and PEG polymers. These values are determined from the retention time of the product eluted from the ion exchange matrix using a linear gradient of buffer. Corrections were made to reflect the time system lag time between the control sequence input and the actual buffer change at the detector. Basically, the retention time of a non-retained MPEG was subtracted from the observed retention time and the salt concentration at that time was calculated based on the slope of the gradient utilized.

TABLE 2

Comparison of Binding of Derivatized PEG and MPEG to Ion Exchange Resin

| MEG/PEG Derivatives | Mp (kDa) | Salt concentration of Eluant (M) | Example # |
|---|---|---|---|
| Succinic acid ester derivatives | | | |
| 20k MPEG | 22.371 | 0.0060 | 6 |
| 30k MPEG | 32.321 | 0.0060 | 6 |
| 8k PEG | 8.632 | 0.0060 | 6 |
| 35k PEG | 36.575 | 0.0060 | 6 |
| phthalate ester derivatives | | | |
| 10k MPEG | 9.270 | 0.0060 | 1 |
| 20k MPEG | 22.371 | 0.0060 | 1 |
| 30k MPEG | 32.321 | 0.0060 | 1 |
| 8k PEG | 8.632 | 0.0060 | 1 |
| 20k PEG | 23.774 | 0.0060 | 1 |
| 35k PEG | 36.575 | 0.0060 | 1 |
| Benzene tricarboxylic acid ester derivatives | | | |
| 10k MPEG isomers 1 & 2* | 9.270 | 0.0590 | 3 |
| 20k MPEG isomers 1 & 2* | 22.371 | 0.0476 | 2 |
| 30k MPEG isomers 1 & 2* | 32.321 | 0.0415 | 4 |
| 8k PEG | 8.632 | 0.1410 | 6 |
| 20k PEG | 23.774 | 0.0807 | 6 |
| 35k PEG | 36.575 | 0.0708 | 6 |
| Benzene tetracarboxylic acid ester derivatives | | | |
| 10k MPEG | 9.270 | 0.2071 | 5 |
| 20k MPEG | 22.371 | 0.1703 | 5 |
| 30k MPEG | 32.321 | 0.1561 | 5 |
| 8k PEG | 8.632 | 0.3555 | 6 |
| 35k PEG | 36.575 | 0.2987 | 6 |

*The averaged values of eluent concentration for the isomers of benzene tricarboxylic acid ester esters are reported.

Figure 12:
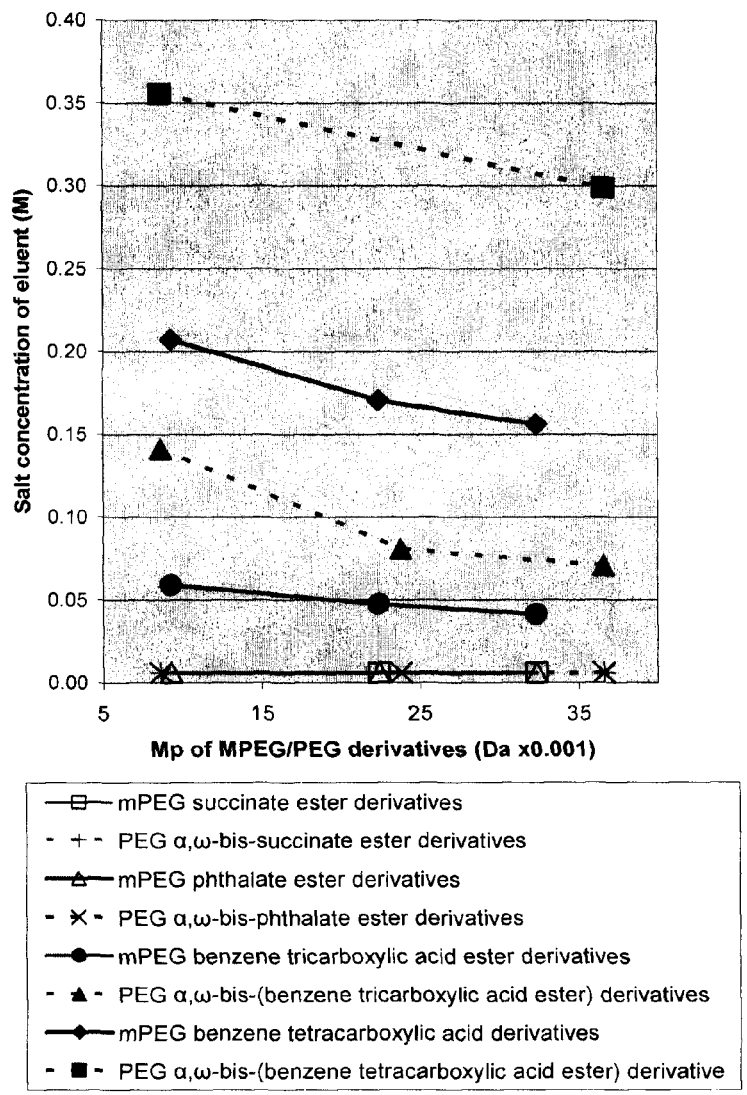
FIG. 12 illustrates the influence of polymer molecular weight and charge on the binding to ion exchange resin as measured by the salt concentration of eluant required to elute the various PEG and MPEG derivatives according to Example 7.

Table 2 and FIG. 12 show derivatives such as MPEG and PEG succinate derivatives known in the prior art for comparative purposes and to demonstrate the great utility of the current invention when compared to these materials. Mono-charged MPEG and PEG polymers listed in the succinic acid ester derivative and phthalate ester derivative categories co-eluted at a low salt concentration level, showing that the mono-charged derivatization does not assist in separating the species of polymers. However, when the polymers are converted to di- or tri-charged derivatives, shown in the benzene tricarboxylic acid ester and benzene tetracarboxylic acid ester categories, the derivatives exhibited elution at higher and distinct salt concentrations.

FIG. 12 is a graphical representation of the salt concentration required to elute a species versus the molecular weight of the polymer derivative being eluted. FIG. 12 illustrates the influence of polymeric molecular weight on salt concentration of ion exchange elutant required to elute the polymeric MPEG and PEG derivatives shown in Table 2 from a SEPAX™ ion exchange column. The stronger the binding, the greater the salt concentration required to elute the polymer.

For polymers derivatized with moieties having more than one charge, the molecular weight of the polymer is inversely correlated to the required salt concentration of the buffer required to elute the polymer derivative. However, for polymers derivatized with mono-charged moieties, there is no such relationship. It can be easily noted that products with two or more ionizable groups need significantly greater concentration of salt to be eluted from the ion exchange matrix compared to the products with less than two ionizable groups. Additionally, when dealing with the derivatizing molecules of the invention, there is significant difference between the buffer concentration required for elution of derivatized MPEG material and the corresponding derivatized PEG material with twice the molecular weight.

In particular, Table 2 and FIG. 12 demonstrate the unexpectedly strong binding of polymers with both terminal groups derivatized according to the invention with a derivatizing molecule capable of possessing two or more ionizable groups after attachment when compared to similar molecular weight species possessing only one identical derivatized terminal group. Such polymers with two ends derivatized with a derivatizing molecule capable of possessing two or more ionizable groups bind more strongly than the mono-substituted polymer with only one half the molecular weight and the same mass to charge ratio.

The number of charges present on water soluble polymers derivatized at their reactive termini affects their behavior with respect to ion exchange chromatography profoundly. Unlike many other physical properties that are only influenced by the charge to mass ratio of such molecules, the observed interaction with the ion exchange material behaves in a more complex manner. Although there is an expected decrease in binding strength observed with a simple increase in molecular weight of a homologous series of polymers (e.g. MPEG derivatives with increasing molecular weight are bound less tightly than smaller MPEG derivatives), other more complex interactions contribute to a greatly enhanced binding of derivatives with more than one termini substituted with a derivatizing molecule capable of possessing two or more ionizable groups after attachment. With derivatives of the invention, FIG. 12 shows the "lines" relating a molecular weight group of derivatives are well separated from the "line" connecting similar weight materials with a different number of reactive termini. That is to say that the MPEG materials with 2 ionizable groups are separated from the PEG materials with 2 ionizable groups. Similarly, the MPEGs with three ionizable groups are even more distinctly separated from the corresponding group of PEG derivatives with both ends derivatized with three ionizable groups.

These data illustrate that polymer derivatization with derivatizing molecules having more than one ionizable group enables ion exchange separation of polymers with different numbers of reactive termini. The binding of a polymer to the resin will vary with such parameters as pH, temperature, and the nature of the resin, etc. The data provided in this example are merely intended to show that separation is achieved, but not to be considered limiting to a particular salt concentration shown or a particular resin.

Example 8

MPEG Maleimide Analysis Via Formation of a Dianionic Addition Product.

To determine the activity of a synthesized maleimide derivatized MPEG, a derivative is prepared by use of a thiol having two carboxylic acid substituents and analyzed via ELSD. MPEG maleimide (20,000 Da, 0.100 g, 0.005 mmol), mercapto succinic acid (0.015 g, 0.1 mmol) and diisopropylethylamine (DIEA, 0.035 mL, 0.2 mmol) were reacted together in anhydrous dichloromethane. The reaction vessel was rotated for 20 hours at ambient temperature.

Figure 13A:
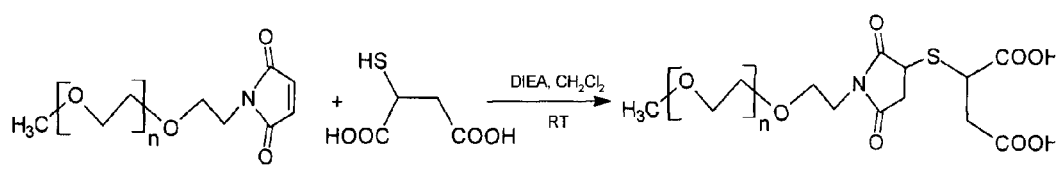
FIG. 13A illustrates a MPEG maleimide derivative forming a diacid product after reaction with a derivatizing molecule of the invention.
Figure 13B:
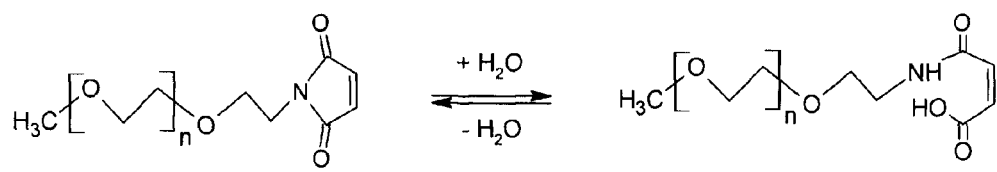
FIG. 13B illustrates the ring opening of MPEG maleimide to MPEG maleamic monoacid.
Figure 14:
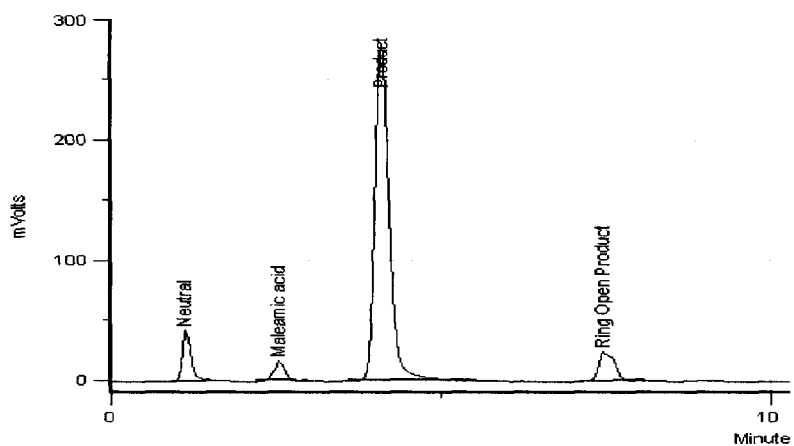
FIG. 14 depicts a chromatogram of a 20,000 Da MPEG maleimide derivative after reaction with mercaptosuccinic acid according to Example 8. The use of a diacid allows separation of all species.

Ion exchange analysis. Analytical ion exchange separation was conducted as follows. A sample (0.330 mL) of the reaction solution was removed from the reaction vessel and reduced to dryness. Ammonium acetate buffer (0.150 mL) was added to dissolve the residue; 0.100 mL of this solution was spin filtered on a prepared Bio-spin Tris 6 filter. The spin-filtered filtrate was diluted with 0.900 mL of 0.0004 M $NH_4OAc$. A 5 µL sample was injected into a mobile phase of Buffer A at a flow rate of 0.9 mL per minute and flowed through a Mono Q™ 4.6/100 PE anion column and detected with an ELSD. After 1 minutes, the elutant was changed to 10% Buffer B and at 5 minutes to 90% Buffer B. FIG. 13A illustrates the maleimide derivatization of MPEG while FIG. 13B illustrates the ring opening of MPEG maleimide to MPEG maleamic monoacid. The chromatogram in FIG. 14 depicts the separation of these mono-, di- and tri-anionic material. The maleamic monoacid has a retention time of 2.56 minutes while the dianion reaction product is more retained and elutes at 4.11 minutes. The most highly retained species is the result of the ring opening of the product which is a trianionic species.

Example 9

Derivatization and Analysis of 20,000 MPEG Amine Utilizing Sulfo Acid Derivatives.

Figure 15:
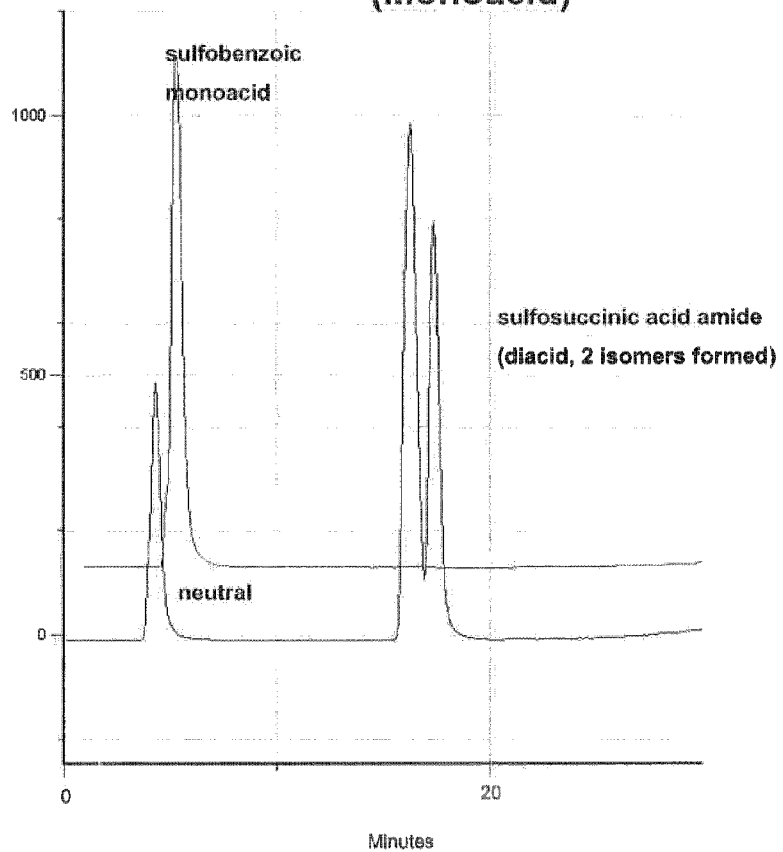
FIG. 15 shows an overlay of MPEG 20,000 Da sulfosuccinic acid amide (diacid)/MPEG 20,000 Da sulfobenzoic acid amide (monoacid) according to Example 9.

MPEG amine (20,000 Da, 1.0 g, 0.05 mmol) and 4-sulfobenzoic acid potassium salt (120 mg, 0.5 mmol) were dissolved in water. 2-{N-morpholino}ethane sulfonic acid (MES, 0.1M, 0.39 g) was added as buffer and the pH was adjusted to 5.6 with sodium hydroxide (0.1N, 1.0 mL). 1-Ethyl-3-(3-dimethylaminopropyl)carbodiimide hydrochloride (EDAC, 96 mg, 0.5 mmol) and N-hydroxylsuccimide (NHS, 144 mg, 1.25 mmol) were added and the solution was stirred at 20° C. for 24 hours. A second addition of EDAC (96 mg, 0.5 mmol) and NHS (144 mg, 1.25 mmol) were added. The solution was extracted with dichloromethane (3×50 mL) and dried over sodium sulphate. The dichloromethane was removed under reduced pressure. The product was precipitated with MTBE. The precipitate was filtered and dried; 0.8820 g resulted (88.2% yield). Similarly, 20,000 Da MPEG amine was reacted with sulfosuccinic acid. FIG. 15 is on overlay of the mono and diacid amide derivatives.

Figure 16:
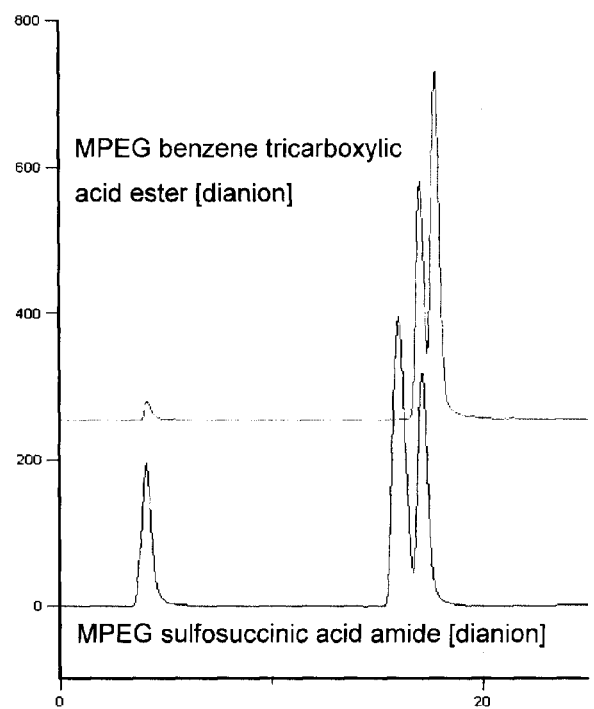
FIG. 16 depicts an overlay MPEG 20,000 Da sulfosuccinic acid amide (diacid)/MPEG 20 000 Da benzene tricarboxylic acid ester (diacid) according to Example 9.

Table 3 compares the retention times of the charged amide derivatives versus the charged ester derivatives. There is no distinction between the two monocharged species or the two bischarged species. FIG. 16 is an overlay of the diacid species, one with two carboxylic acid groups and one with one carboxylic acid group and one sulfonic acid ionizable group. The separation depends largely on the number of ionizable groups, not their nature.

TABLE 3

Comparison of Retention Times for various Polymers and Derivatizing Molecules

| Starting PEG | Reactant | Results |
|---|---|---|
| MPEG-amine | 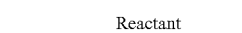<br>4-sulfobenzoic acid | <br>Retention time: 4.35 min |

TABLE 3-continued

Comparison of Retention Times for various Polymers and Derivatizing Molecules

| Starting PEG | Reactant | Results |
| --- | --- | --- |
| MPEG-OH | 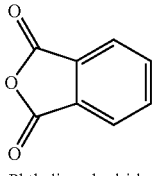 Phthalic anhydride | 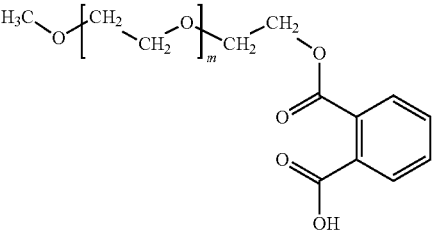 Retention time: 4.21 min |
| MPEG-amine | 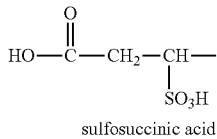 sulfosuccinic acid | 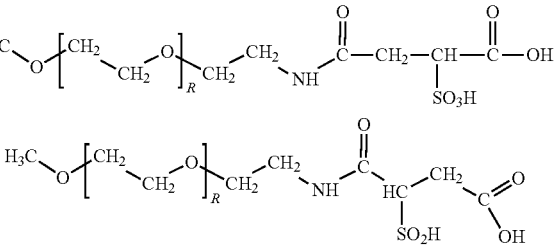 Retention time of isomers: 16.16 & 17.27 min |
| MPEG-OH | 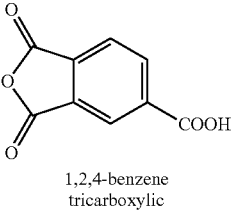 1,2,4-benzene tricarboxylic anhydride | 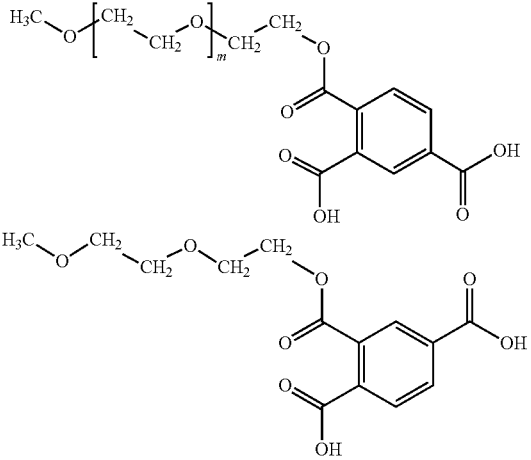 Retention time of isomers: 17.01 & 17.73 min |

Example 10

Analysis of Reductive Amination Products of 30,000 Da MPEG Propionaldehyde.

Figure 17:
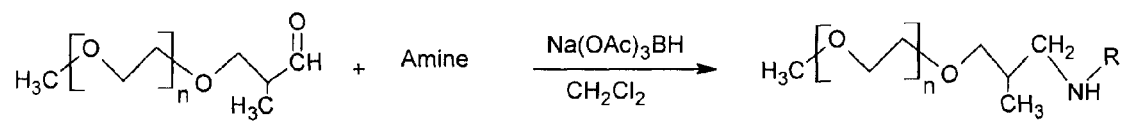
FIG. 17 depicts a reaction schema used in Example 10.

The result of the reductive amination of MPEG propionaldehyde is used as a measure of the propionaldehyde activity, as depicted in the schema for FIG. 17. MPEG propionaldehyde (30,000 Da, 0.150 g) and 4-methoxybenzyl amine (0.013 mL, 0.1 mmol) were mixed in anhydrous dichloromethane (4 mL) and then treated with sodium triacetoxyborohydride (0.150 mL of suspension of 40 mg/mL). The reaction was allowed to stir for eight hours. An aliquot was removed, stripped to dryness and prepared for analysis. Similarly, 30,000 Da MPEG propionaldehyde was reacted with dimethylaminopropyl amine. Other molecular weight MPEG propionaldehydes were similarly reacted. These reductive amination reactions with 4-methoxybenzyl amine and dimethylaminopropyl amine yield products which possess, respectively mono and di cation groups.

Figure 18:
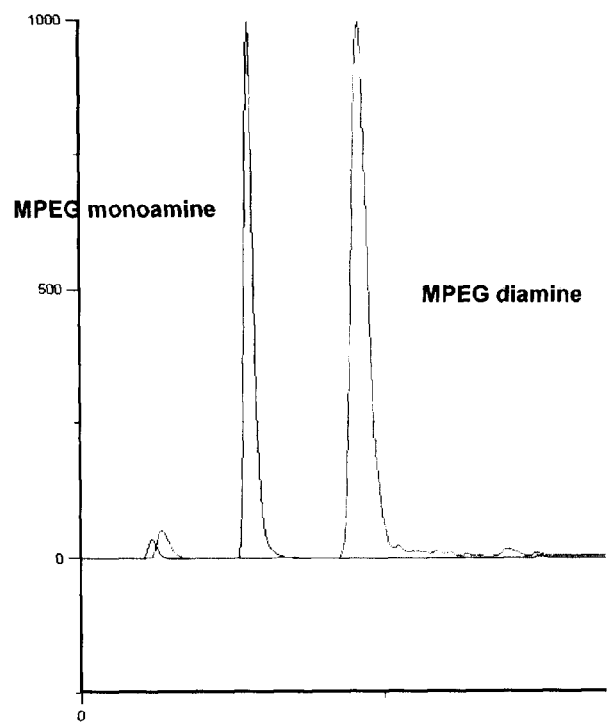
FIG. 18 depicts an overlay MPEG 30,000 Da methoxybenzylamine (monoamine) and MPEG 30 000 Da dimethylaminiopropylamine (diamine) according to Example 10.

Analytical ion exchange separation: A sample (0.330 mL) of the reaction solution was removed from the reaction vessel and reduced to dryness. Ammonium acetate ($NH_4OAc$) buffer (0.150 mL) was added to dissolve the residue; 0.100 mL of this solution was spin filtered on a prepared Bio-spin Tris 6 filter. The spin-filtered filtrate was diluted with 0.900 mL of 0.4 mM $NH_4OAc$. A 10 µL sample was injected into a mobile phase of 0.0004M ammonium acetate buffer (Buffer A) and of 0.4M ammonium acetate buffer (Buffer B) at a flow rate of 0.9 mL per minute and flowed through a Mono S™ 4.6/100 PE cation column and detected with an evaporative light scattering detector. FIG. 18 is an overlay of the two propionaldehyde reductive animation products. The product, 30,000 Da MPEG 4-methoxybenzyl amine possessing a monocationic charge, is much less strongly bound to the resin than the product 30,000 Da MPEG 3-N,N-dimethylaminopropylamine possessing a dicationic charge.

Example 11

Synthesis and Purification of 35,000 Da EtO-PEG-OH Utilizing 1,2,4-Benzenetricarboxylic Anhydride.

Figure 19:
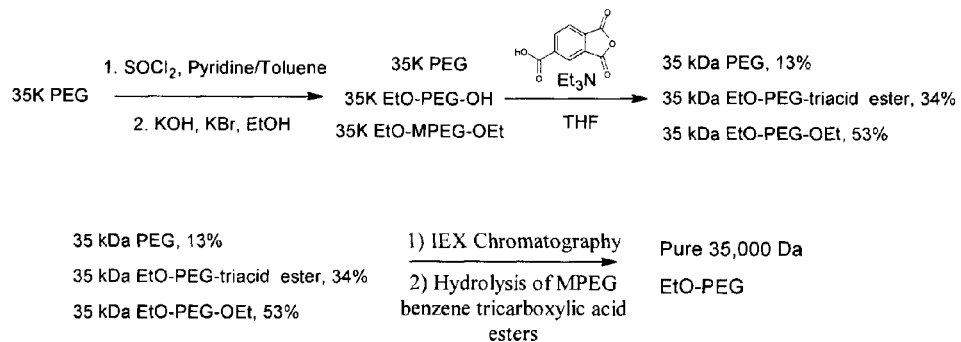
FIG. 19 depicts the route for the new synthesis and purification of lower alkyl PEG monoethers from PEG according to Example 11.
Figure 19:
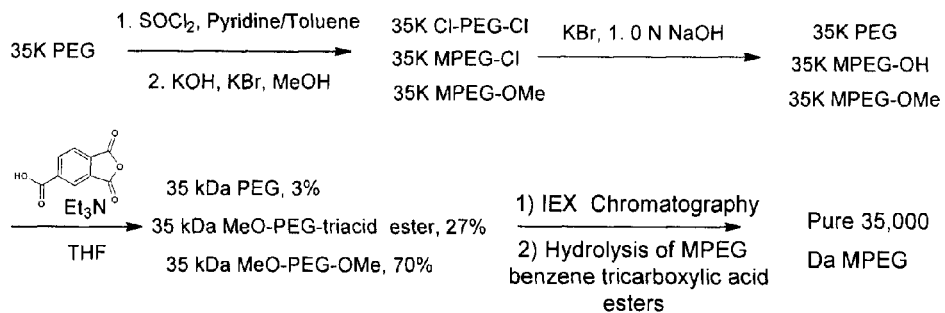

Preparation of 35,000 Da EtO-PEG benzene tricarboxylic acid ester. PEG (35,000 Da, 10.0 g, 0.286 mmol) was combined with toluene (120 mL), heated to reflux and the distillate (20 mL) removed via Dean-Stark trap. The mixture was then cooled to 60° C. and treated with pyridine (0.139 mL, 1.72 mmol) and $SOCl_2$ (0.376 mL, 5.15 mmol). After 30 minutes, the mixture was heated to reflux and the distillate (60 mL) removed from the trap. The mixture was then cooled again to 70° C. and ethanol (1.67 mL, 28.6 mmol) was then added followed by potassium bromide (0.341 g, 2.86 mmol) and potassium hydroxide (0.357 g, 5.73 mmol). After 16 hours, $^1$H-NMR showed the presence of EtO-PEG-OH. A portion of the isolated product (4.02 g) was dissolved in THF and treated with 1,2,4-benzenetricarboxylic anhydride (0.22 g, 1.15 mmoles.) and triethylamine (32 ml, 0.23 mmol) for 16 hours. The material was isolated by extraction/precipitation. FIG. 19 describes this synthesis.

Purification of the unpurified EtO-PEG benzene tricarboxylic acid ester. Q-Sepharose Fast Flow ion exchange resin (50 mL) was used for purification of the PEG benzene tricarboxylic acid ester. Prior to loading the unpurified MPEG benzene tricarboxylic acid ester, the resin was regenerated with 375 mM ammonium acetate solution (5.2 kg ammonium acetate/180 L deionized water) and washed with deionized water until the conductivity measurements are less than 0.020 milli-Seimens. A solution of unpurified EtO-PEG benzene tricarboxylic acid ester 20 000 Da in deionized water (1.0 g/25 mL DI water=40 mg/mL) was prepared and loaded onto the prepared column at a flow rate 4 mL/min. The neutral PEG was eluted with 60 mL of deionized water. After a negative cobalt test result indicating that all neutral material had been washed off, the product was eluted with a 4 mM ammonium acetate solution at the same flow rate. The eluate was collected from the column in 10 mL fractions. Each fraction was tested using the cobalt test. Product was present in 30 mL of eluate.

Figure 20:
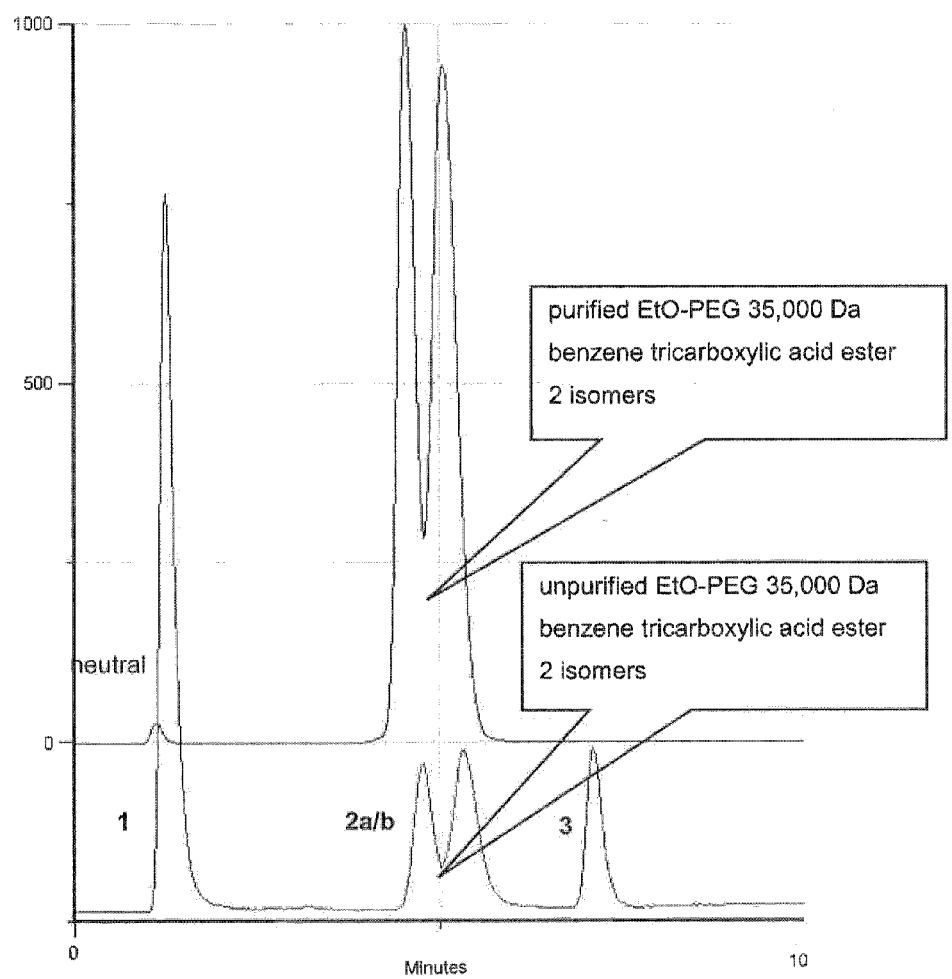
FIG. 20 depicts an overlay unpurified EtO-PEG 35,000 Da benzene tricarboxylic acid ester & purified EtO-PEG 35,000 Da benzene tricarboxylic acid ester according to Example 11.

Ion exchange analysis. FIG. 20 is an overlay of the unpurified material and the purified collected fraction using a typical two step gradient elution method. The unpurified material contained 34% of desired MPEG benzene tricarboxylic acid ester product (peaks 2a/b), The PEG α,ω-bis-(benzene tricarboxylic acid ester) derivatized material (13%, peak 3) was more retained. The α,ω-bis-(ethoxy) PEG 35,000 Da neutral and underivatized material (peak 1) represented 53% of the mixture.

Preparation of deprotected purified EtO-PEG. Fractions containing desired purified EtO-PEG benzene tricarboxylic acid ester were combined, treated with sodium hydroxide (1N, 5 mL) and the volume reduced to 20 mL with a slow distillation of the solvent under reduced pressure. Hydrochloric acid solution was added to the solution until a pH of 6.1 was achieved. The product was extracted into dichloromethane (2×25 L); the organic layer was collected and dried over anhydrous sodium sulfate. The filtrate was collected and the volume of dichloromethane was reduced by vacuum distillation. MTBE was added and a precipitate formed. The resultant precipitate was collected by filtration and dried. Overall yield of the purified EtO-PEG 35,000 Da (0.23 g) was 63%.

Example 12

Synthesis and Analysis of 35,000 Da MPEG Utilizing 1,2,4-Benzenetricarboxylic Anhydride.

Figure 21:
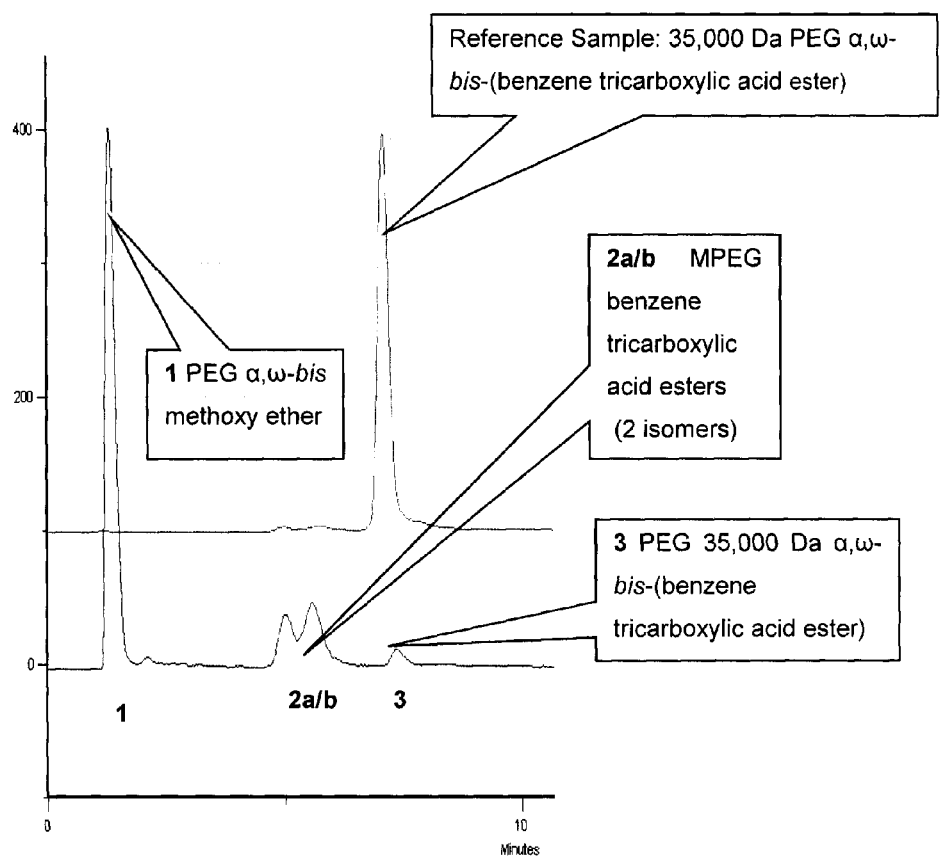
FIG. 21 depicts the chromatography of MPEG benzene tricarboxylic acid ester prepared according to Example 12. A chromatogram of a reference preparation of 35,000 PEG α,ω-bis-(benzene tricarboxylic acid ester) is also shown.

Preparation of MPEG benzene tricarboxylic acid ester. PEG (35,000 Da, 10.0 g, 0.286 mmol) was combined with toluene (120 mL), heated to reflux and the distillate (20 mL) removed via dean-stark trap. The mixture was then cooled to 60° C. and treated with pyridine (0.138 mL, 1.12 mmol) and thionyl chloride (0.612 g, 5.15 mmol). After 30 minutes, the mixture was heated to reflux and the distillate (60 mL) removed from the trap. The mixture was then cooled again to 50° C. and methanol (1.16 mL, 28.6 mmol) was then added followed by potassium bromide (0.34 g, 2.86 mmol) and potassium hydroxide (0.357 g, 5.72 mmol). After 16 hours, $^1$H-NMR (benzene) showed the presence of 54% methoxylated PEG. $^1$H-NMR (DMSO) showed no $CH_2OH$ proton. A 15% sodium chloride solution (100 mL) was then added and the reaction mixture acidified with 1.0N hydrochloric acid. The resulting solution was extracted with dichloromethane (3×30 mL), dried over sodium sulphate, filtered, concentrated and precipitated with MTBE to give a white solid (8.6 g). A portion of the solid (1.6 g) containing PEG dichloride, MPEG chloride and dimethoxy PEG was stirred at room temperature for 72 hours with potassium bromide (0.218 g, 1.83 mmol) in 1.0N sodium hydroxide (16 ml). After acidification, extraction, concentration and precipitation, a white solid (1.3 g) was obtained. The solid was dissolved in THF and treated with 1,2,4-benzenetricarboxylic anhydride (0.128 g, 0.645 mmol) and triethylamine (0.018 mL, 0.129 mmol). After 16 hours, the reaction mixture was concentrated, redissolved in 15% sodium chloride solution (15 mL) and acidified with 1.0 N hydrochloric acid. The resulting solution was extracted with dichloromethane (3×10 mL), dried over sodium sulphate, filtered, concentrated and precipitated with MTBE to give a white solid (600 mg). FIG. 21 [depicts the chromatography of MPEG benzene tricarboxylic acid ester. A chromatogram of a reference preparation of 35,000 PEG α,ω-bis-(benzene tricarboxylic acid ester) is also shown.

The above-described embodiments of the invention are intended to be examples only. Alterations, modifications and variations can be effected to the particular embodiments by those of skill in the art without departing from the scope of the invention, which is defined solely by the claims appended hereto.

What is claimed is:

1. A process for the separation of a water-soluble poly(ethylene oxide) (PEO) polymer of interest from other water-soluble poly(ethylene oxide) polymers, initially present as one component of a mixture, wherein the polymer of interest contains a different number of reactive terminal groups than the other water-soluble polymers in the mixture, wherein said reactive terminal groups are hydroxyl, sulfhydryl, mercapto, halide, carboxylate, amino, aldehyde, maleimide, or —$CH_2$—X wherein X is a halide or sulfonic acid ester, said process comprising:

reacting the initial mixture of polymers to covalently bind the reactive terminal group with a derivatizing molecule, said derivatizing molecule being capable of forming a covalent bond with said reactive terminal group, wherein said derivatizing molecule has 2 or 3 ionizable groups after the covalent binding, and wherein said 2 or 3 ionizable groups are all independently selected from the group consisting of carboxylate, phosphate, phosphonate, borate, sulfonate, and sulfate groups, or wherein said 2 or 3 ionizable groups are all independently selected from the group consisting of amine, aromatic amine, and heterocyclic nitrogen containing groups; and subjecting the reacted polymer mixture to ion exchange to separate the derivatized (PEO) polymer of interest from the other derivatized PEG polymers.

2. The process of claim 1, wherein the polymer of interest is monomethoxy poly(ethylene glycol) (MPEG).

3. The process of claim 2, wherein the initial mixture of polymers comprises monomethoxy poly(ethylene glycol) (MPEG) and poly(ethylene glycol) (PEG).

4. The process of claim 3, wherein the initial mixture of polymers comprises less than 10% PEG.

5. The process of claim 3, additionally comprising, prior to the step of reacting the initial mixture of polymers, the step of preparing MPEG by ethylene oxide polymerization thereby forming a mixture of polymers containing MPEG and PEG.

6. The process of claim 1, wherein:
the polymer of interest is mono alkyl ether end capped poly(ethylene glycol); and
the other polymers comprises one or both of poly(ethylene glycol) or bis alkyl ether end capped poly(ethylene glycol).

7. The process of claim 6, wherein the polymer of interest is methoxy ether end capped poly(ethylene glycol).

8. A method for analysis of the presence of more than one water-soluble poly(ethylene oxide) polymers in an initial mixture of water-soluble poly(ethylene oxide) polymers, wherein each polymer to be assessed has a different number of reactive terminal groups, the method comprising the steps of:
carrying out the process of claim 1; and
evaluating polymer composition of the reacted polymer mixture.

9. The method of claim 8, wherein the step of evaluating polymer content is used to demonstrate that the initial mixture contains predominantly one polymer of interest and a negligible amount of contaminant polymers.

10. The method of claim 8, wherein the step of evaluating polymer content is used to determine content of a reactive polymer wherein only a polymer possessing a particular reactive termini can be converted to a derivatized polymer.

11. The method of claim 8, wherein the step of evaluating polymer content is used to determine presence or amount of any polymer in the mixture that can react more than once with the derivatizing molecule.

12. The method of claim 11, wherein the amount of a reactive product formed from a PEG species present in a reactive MPEG polymer is measured.

13. The process of claim 1, wherein the reaction with the derivatizing molecule results in essentially all reactive terminal groups of the water-soluble poly(alkylene oxide) polymers being covalently bound to a di-anion or a tri-anion.

14. The process of claim 1, wherein the reactive terminal groups are hydroxyl groups.

15. The process of claim 1, further comprising removing the derivatizing molecule from the polymer of interest and/or the other polymers after the step of separating.

16. The process of claim 1, wherein the resulting separated polymer of interest, is greater than about 99% pure.

17. The process of claim 1, wherein the ethylene oxide monomeric moieties are independently selected from the group consisting of ethylene oxides of structure:

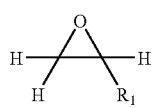

wherein $R_1$ is H or a $C_{1-4}$-alkyl group.

18. The process of claim 17, wherein $R_1$ is H or methyl.

19. The process of claim 1, wherein the initial mixture of polymers each has an average size of about 100,000 Da or less.

20. The process of claim 1, wherein the initial mixture of polymers each has an average size of about 9,000 Da or greater.

21. The process according to claim 1, wherein:
the polymer of interest is a poly(ethylene glycol) polymer having one reactive terminal group;
the initial mixture of polymers comprises a poly(ethylene glycol) polymer having two reactive terminal groups admixed with the polymer of interest;
the step of reacting comprises acylation with the derivatizing molecule; and
ion exchange chromatography is employed to elute a fraction containing the polymer of interest at a distinct ionic strength.

22. The process of claim 1, wherein the polymer of interest is MPEG, and wherein the process comprises, prior to the step of reacting the initial mixture of polymers, the step of preparing MPEG from PEG and methanol.

23. The process of claim 1, wherein the polymer of interest is poly(ethylene glycol) monoethyl ether (EtO-PEG), and wherein the process comprises, prior to the step of reacting the initial mixture of polymers, the step of preparing EtO-PEG from PEG and ethanol.

24. The process of claim 1, wherein the derivatizing molecule is mercaptosuccinic acid.

25. The process of claim 1, wherein the derivatizing molecule is dimethylaminopropylamine.

26. A process for the separation of a water-soluble poly (ethylene oxide) polymer (PEG) of interest from other water-soluble poly(ethylene oxide) polymers, initially present as one component of a mixture, wherein the polymer of interest contains a different number of reactive terminal groups than the other water-soluble polymers in the mixture, wherein said reactive terminal groups are hydroxyl, sulfhydryl, mercapto, halide, carboxylate, amino, aldehyde, maleimide, or —$CH_2$—X wherein X is a halide or sulfonic acid ester, said process comprising:
reacting the initial mixture of polymers to covalently bind the reactive terminal group with a derivatizing molecule, said derivatizing molecule being capable of forming a covalent bond with said reactive terminal group, wherein said derivatizing molecule has 2 or 3 ionizable groups after the covalent binding, and wherein said 2 or 3 ionizable groups are all independently selected from the group consisting of carboxylate, phosphate, phosphonate, borate, sulfonate, and sulfate groups, or wherein said 2 or 3 ionizable groups are all independently selected from the group consisting of amine, aromatic amine, and heterocyclic nitrogen containing; and
subjecting the reacted polymer mixture to ion exchange to separate the derivatized (PEG) polymer of interest from the other derivatized PEG polymers:
wherein the derivatizing molecule is 1,2,4-benzene tricarboxylic acid anhydride, 1,2,4,5-benzene tetracarboxylic acid dianhydride, 1,2,3,4-cyclobutane tetracarboxylic acid dianhydride, or 2,2',3,3'-dicarboxybenzophenone dianhydride.

* * * * *